US010709662B1

(12) United States Patent
Ahmed et al.

(10) Patent No.: US 10,709,662 B1
(45) Date of Patent: Jul. 14, 2020

(54) MUCOADHESIVE BUCCAL FILM HAVING A DUAL RELEASE CARRIER SYSTEM

(71) Applicants: King Abdulaziz University, Jeddah (SA); Virginia Commonwealth University, Richmond, VA (US)

(72) Inventors: Tarek A. Ahmed, Jeddah (SA); Alaa O. Bawazir, Jeddah (SA); Abdelsattar M. Omar, Jeddah (SA); Martin K. Safo, Richmond, VA (US)

(73) Assignees: King Abdulaziz University, Jeddah (SA); Virginia Commonwealth University, Richmond, VA (US)

( * ) Notice: Subject to any disclaimer, the term of this patent is extended or adjusted under 35 U.S.C. 154(b) by 0 days.

(21) Appl. No.: 16/775,304

(22) Filed: Jan. 29, 2020

(51) Int. Cl.
*A61K 9/00* (2006.01)
*A61K 47/40* (2006.01)
*A61K 47/32* (2006.01)
*A61K 9/107* (2006.01)
*A61K 47/24* (2006.01)
*A61K 31/351* (2006.01)
*A61K 9/14* (2006.01)
*A61P 1/16* (2006.01)

(52) U.S. Cl.
CPC ............ *A61K 9/006* (2013.01); *A61K 9/1075* (2013.01); *A61K 9/146* (2013.01); *A61K 31/351* (2013.01); *A61K 47/24* (2013.01); *A61K 47/32* (2013.01); *A61K 47/40* (2013.01)

(58) Field of Classification Search
CPC ........ A61K 9/006; A61K 47/40; A61K 47/32; A61K 9/1075; A61K 47/24; A61K 31/351; A61K 9/146; A61P 1/16
See application file for complete search history.

(56) References Cited

U.S. PATENT DOCUMENTS

2003/0113367 A1  6/2003  Penkler

FOREIGN PATENT DOCUMENTS

| CA | 2 595 485 | | 2/2009 |
| CN | 102028658 A | * | 4/2011 |

OTHER PUBLICATIONS

Google English Translation of CN102028658A ([retrieved from on-line website: https://patents.google.com/patent/CN102028658A/en, last visit Apr. 6, 2020]). (Year: 2011).*
Kumar et al., "The Potential of Statins for Buccal Delivery", Journal of Molecular Pharmaceutics & Organic Process Research, vol. 2, issue 1, 2014, pp. 1-7. (Year: 2014).*
Cui et al., "Effect of beta-cyclodextrin complexation on solubility and enzymatic hydrolysis rate of icariin", J Nat Sci Biol Med. Jan.-Jun. 2013; 4(1): 201-206.

(Continued)

*Primary Examiner* — Kyung S Chang
(74) *Attorney, Agent, or Firm* — W & C, IP

(57) ABSTRACT

Mucoadhesive buccal films comprising a statin-hydroxypropyl-beta-cyclodextrin inclusion complex and a statin-loaded mixed micelle composition, wherein the ratio of the mixed micelle composition to the inclusion complex is from 2:0.5 to 2:1.5 are provided. Methods of improving permeation of a statin across mucosal tissue by administering the film to a subject are also provided.

9 Claims, 9 Drawing Sheets
(4 of 9 Drawing Sheet(s) Filed in Color)

(56) References Cited

OTHER PUBLICATIONS

Dias et al., "The effect of beta-cyclodextrins on the permeation of diclofenac from supersaturated solutions", Int J Pharm. Sep. 16, 2003;263(1-2):173-81.

Guo et al., "Comparison of bile salt/phosphatidylcholine mixed micelles in solubilization to sterols and stability", Drug Design, Developement and Therapy, Nov. 17, 2016:10 3789-3798.

Gurten et al., "Complexation and enhancement of temozolomide solubility with cyclodextrins", BJPS 2018;54(2): e17513.

Jagdale et al., "Dissolution Rate Enhancement, Design and Development of Buccal Drug Delivery of Darifenacin Hydroxypropyl beta-Cyclodextrin Inclusion Complexes", Journal of Pharmaceutics, 2013, 983702.

Jun et al., "Preparation and characterization of simvastatin/hydroxypropyl-beta-cyclodextrin inclusion complex using supercritical antisolvent (SAS) process", Eur J Pharm Biopharm. Jun. 2007;66(3):413-21.

Kumbhar et al., "Simvastatin Loaded Nano Mixed Micelles: An Approach to Treat Hormone Dependent Carcinomas", IJPSR (2019), vol. 10, issue 2: 546-554.

Lichtenberg et al., "On the solubility of calcium deoxycholate: kinetics of precipitation and the effect of conjugated bile salts and lecithin", Chem Phys Lipids, Apr. 1988; 46(4):279-91.

Lv et al., "Mucoadhesive buccal films containing phospholipid-bile salts-mixed micelles as an effective carrier for Cucurbitacin B delivery", Drug Delivery (2014), 22:3, 351-358.

Rupp et al., "Mixed micelle formation with phosphatidylcholines: the influence of surfactants with different molecule structures", Int J Pharm. Mar. 15, 2010;387(1-2):120-8.

Tarai et al., "Novel, bucco-compatible simvastatin buccal film: An integrative study of the effect of formulation variables", JSIR 2013; 2(5): 903-913.

* cited by examiner

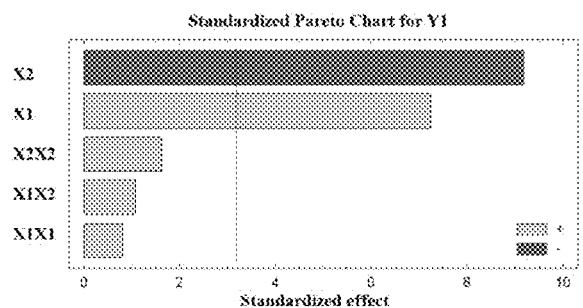 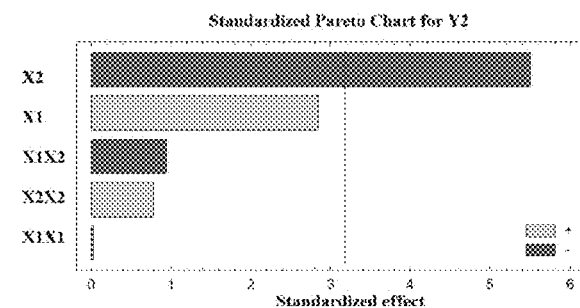
FIG. 9A  FIG. 9B
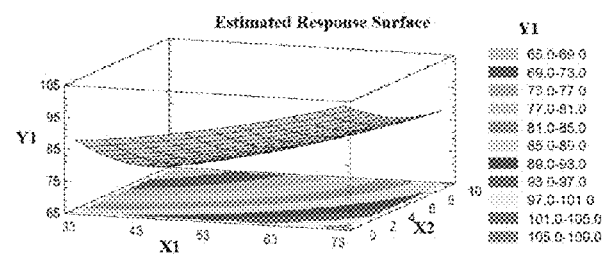
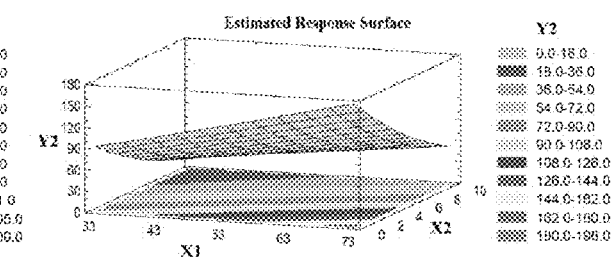
FIG. 9C

US 10,709,662 B1

MUCOADHESIVE BUCCAL FILM HAVING A DUAL RELEASE CARRIER SYSTEM

FIELD OF THE INVENTION

The invention is generally related to buccal films comprising two drug carrier systems, a polymeric drug inclusion complex and mixed micelles, for the enhanced delivery of drugs such as statins.

BACKGROUND OF THE INVENTION

Statins are indispensable for lowering blood cholesterol levels and are increasingly being used to manage cardiovascular disorders, a major cause of death and morbidity around the world [1]. However, many statins suffer from poor solubility and thus low bioavailability.

Different strategies have been reported to improve drug solubility and dissolution in order to achieve a suitable systemic drug concentration and a desired pharmacological effect. These strategies can be classified into physical, chemical and other miscellaneous modifications techniques [6]. Reduction in a drug's particle size by micronization and nanosuspension formation, crystalline change by polymorph and amorphous/crystallin modifications, drug dispersion in hydrophilic carriers (solid dispersions), solid solutions and cryogenic methods are examples of physical modifications [7-11]. Derivatization, salt formation and complexation are common types of chemical modifications [12,13]. Cosolvency, hydrotropes, addition of surfactants and solubilizers, and supercritical fluid technology are good examples of other modifications [14-16].

Mucoadhesive buccal films are pharmaceutical dosage forms that utilize a water-dissolving polymer that allows the prepared films to quickly hydrate, adhere and dissolve when placed in the buccal, palatal, gingival, lingual, sublingual or cheek mucosa of the buccal cavity [20,21]. They are promising drug delivery systems that release their drug content directly toward the buccal mucosa with subsequent drug absorption through the venous blood system that drains from the cheek. Accordingly, development of these films has the advantage of avoiding the hepatic first pass effect [22].

Due to the bioavailability problems with oral delivery of statins, alternative and effective drug delivery systems are needed.

SUMMARY

An aspect of the disclosure provides a mucoadhesive buccal film comprising a crosslinked polyacrylic acid polymer, wherein the film is loaded with a statin-hydroxypropyl-beta-cyclodextrin inclusion complex; and a statin-loaded mixed micelle composition, wherein the ratio of the mixed micelle composition to the inclusion complex is from 2:0.5 to 2:1.5. In some embodiments, the ratio of the mixed micelle composition to the inclusion complex is 2:1. In some embodiments, the statin is simvastatin. In some embodiments, the ratio of the statin to hydroxypropyl-beta-cyclodextrin is 1:2. In some embodiments, the mixed micelle composition comprises phosphatidylcholine (PC) and sodium deoxycholate (SDC). In some embodiments, the ratio of PC to SDC is 1:0.8. In some embodiments, the crosslinked polyacrylic acid polymer is prop-2-enoic acid. In some embodiments, the crosslinked polyacrylic acid polymer is at a concentration of 3-5% w/v.

Another aspect of the disclosure provides a method of improving permeation of a statin across mucosal tissue, comprising providing to a subject in need thereof a film as described herein. In some embodiments, the subject has hypercholesterolemia.

BRIEF DESCRIPTION OF THE DRAWINGS

The patent or application file contains at least one drawing executed in color. Copies of this patent or patent application publication with color drawings will be provided by the Office upon request and payment of the necessary fee.

FIG. 9A-C. Standardized Pareto charts and estimated response surface plots for the effect of the studied factors on (A) $Y_1$, (B) $Y_2$, and (C) $Y_3$.

Figure 1:
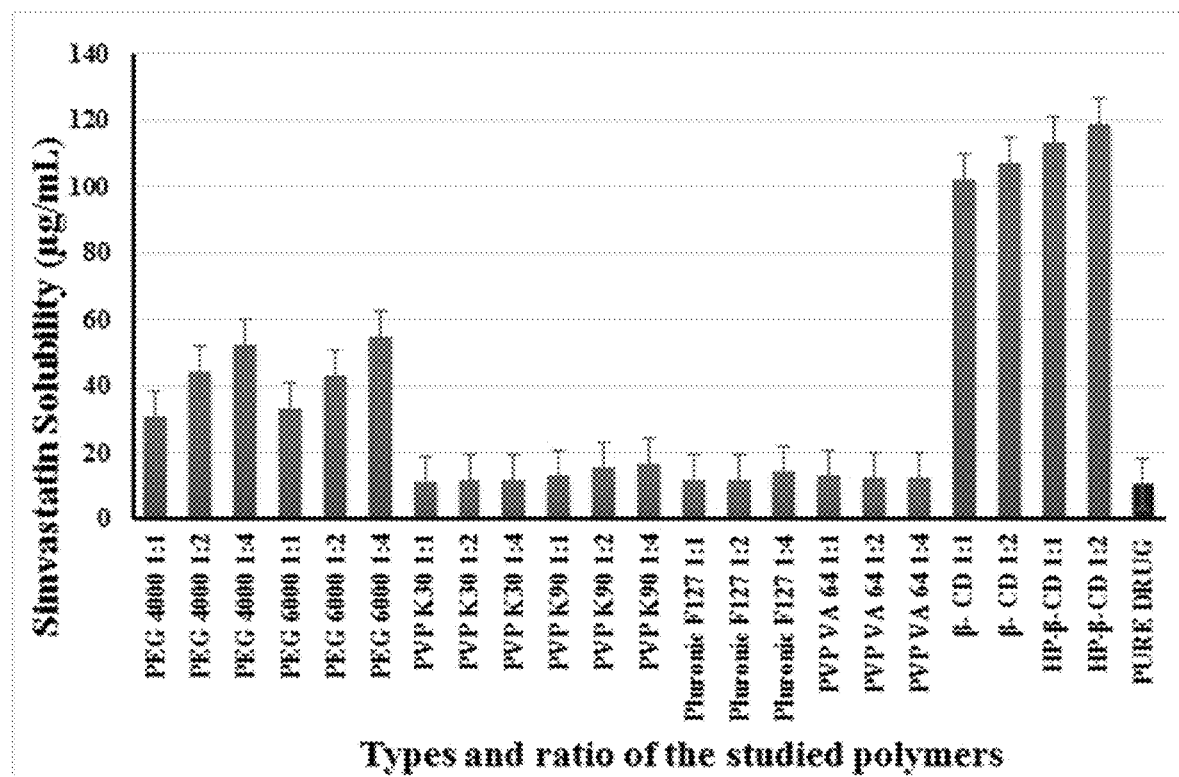
FIG. 1. Solubility of simvastatin with different polymers in different ratios.

The patent or application file contains at least one drawing executed in color. Copies of this patent or patent application publication with color drawings will be provided by the Office upon request and payment of the necessary fee.

DETAILED DESCRIPTION

Embodiments of the disclosure provide a mucoadhesive buccal film loaded with a poorly soluble drug in the form of a cyclodextrin inclusion complex and in the form of mixed micelle carriers as an efficient drug delivery system with enhanced drug ex vivo permeation. The developed mucoadhesive buccal film enhances the drug bioavailability and is an alternative to currently available marketed oral tablets for poorly soluble drugs.

Inclusion complexes are non-covalent associations of molecules in which a molecule of one compound, called the host, has a cavity in which a molecule of another compound, called a guest is included. Formation of an inclusion complex is a useful method for insertion of a hydrophobic drug molecule or the nonpolar portion of a water insoluble drug molecule (known as the guest) into the cavity of a hydrophilic polymer (known as the host). Embodiments of the disclosure include the use of cyclodextrins as host polymers. Cyclodextrins are a group of compounds consisting of, or derived from, the three parent cyclodextrins—alpha-, beta- and gamma-cyclodextrins. Cyclodextrins have numerous uses based on their ability to solubilize complex chemicals. Alpha-, beta- and gamma-cyclodextrins are simple oligosaccharides consisting of six, seven, or eight glucose residues, respectively, connected to macrocyles by alpha (1 to 4) glycosidic bonds. Each of the glucose residues of a cyclodextrin contains one primary (O6) and two secondary hydroxyls (O2 and O3) which can be substituted, for example, methylated. Many cyclodextrin preparations in practical use are mixtures of chemically individual derivatives in which only a part of hydroxyl groups were substituted and which differ in number and position of these substituents. In some embodiments, the cyclodextrin used to form the inclusion complex is hydroxypropyl-beta-cyclodextrin (HP-βCD).

Surfactants have also been utilized to improve the dissolution of poorly water-soluble drugs. When the concentration of the surfactant molecules exceeds their critical micelle concentration (0.05-0.10% for most surfactants), micelle formation occurs. Hydrophobic drugs can be entrapped within the micelle core in a process called micellization which generally results in improving drug solubility and its bioavailability. As used herein, the term "micelle" refers to an aggregate (or cluster) of surfactant molecules. Micelles can exist in different shapes, including spherical, cylindrical, and discoidal. A micelle comprising at least two different molecular species is a mixed micelle. The small size of micelles (typically about 10 nm to about 100 nm) allows for efficient accumulation of an associated active moiety into targeted tissues. Micelles can be formed from one or more polymeric nonionic surfactants.

Embodiments of the disclosure include mixed micelle compositions comprising a bile salt, such as sodium deoxycholate (SDC), and phosphatidylcholine (PC). Bile salts are made of bile acids that are conjugated with glycine or taurine and are important for solubilizing dietary fats in the small intestine. Other suitable bile salts include the sodium and potassium salts of cholic acid, deoxycholic acid, lithocholic acid, and chenodeoxycholic acid. In some embodiments, the ratio of PC to SDC or other bile salt is about 1:0.5 to about 1:1.5, e.g. about 1:0.8.

Other suitable surfactants that are compatible with the micelle compositions described herein include eg. phospholipids, polysorbates, sorbitan esters of fatty acids, cetearyl glucoside or poloxamers or other stabilisers such as xanthan gum, or propylene glycol alginate. Preferably, the total amount of surfactants in the micelle compositions of the presently disclosed embodiments is about 30 percent or less of the total composition with the remaining major component being water.

The present disclosure provides the use of a polymeric inclusion complex and a mixed micelle composition, each being incorporated onto a film, for delivery of a substantially insoluble or sparingly soluble biologically active agent to a human or non-human animal subject. In some embodiments, the active agent has a solubility in water (w/v) which is 3% or less, e.g. 1% or less. In some embodiments, the active agent is a statin, such as simvastatin, atorvastatin, fluvastatin, lovastatin, pitavastatin, pravastatin, and rosuvastatin. Other example of active agents, that are not statins, of poor aqueous solubility are Mefenamic acid, Aripiprazole, Glimepiride, Vinpocetine, Vardenafil, Meloxicam, Lamotrigine, Itraconazole, Dexamethasone and Repaglinide. In some embodiments, the amount of active agent incorporated into the micelle composition is 5-100 mg.

Simvastatin is widely used in the treatment of hypercholesterolemia and dyslipidemia. SMV is a prodrug that converts in the body into an active metabolite and competitively inhibits the activity of the enzyme hydroxymethylglutaryl-coenzyme A (HMG-CoA) Reductase [2]. This enzyme catalyzes the conversion of HMG-CoA to mevalonic acid, the effect which results in inhibition of the endogenous production of cholesterol in the liver. SMV is a poorly water-soluble drug with short half-life of 2 h. It is commercially available as tablets of different strength, such as 5, 10, 20, 40 and 80 mg. Due to intensive first-pass metabolism and poor drug aqueous solubility (6.3 μg/mL, pH 1-7, at 25° C.) orally administered SMV tablets only result in about 5% bioavailability [3].

The ratio of mixed micelles to inclusion complex that may be incorporated onto the film may be from about 2:0.5 to about 2:1.5, e.g. about 2:1.

The term "film" includes thin films and sheets, in any shape, including rectangular, square, or other desired shape. The films described herein may be any desired thickness and size such that it may be placed into the oral cavity of the user. For example, the films may have a relatively thin thickness of from about 1 to about 300 μm, or they may have a somewhat thicker thickness of from about 300 to about 800 μm. For some films, the thickness may be even larger Films may be in a single layer or they may be multi-layered, including laminated films.

Oral dissolving films generally fall into three main classes: fast dissolving, moderate dissolving and slow dissolving. Fast dissolving films generally dissolve in about 1 second to about 30 seconds in the mouth. Moderate dissolving films generally dissolve in about 1 to about 30 minutes in the mouth, and slow dissolving films generally dissolve in more than 30 minutes in the mouth. Fast dissolving films may consist of low molecular weight hydrophilic polymers (i.e., polymers having a molecular weight between about 1,000 to 9,000, or polymers having a molecular weight up to 200,000). In contrast, slow dissolving films generally have high molecular weight polymers (i.e., having a molecular weight in the millions).

Moderate dissolving films tend to fall in between the fast and slow dissolving films. Moderate dissolving films dissolve rather quickly, but also have a good level of mucoadhesion. Moderate dissolving films are also flexible, quickly wettable, and are typically non-irritating to the user. Such moderate dissolving films provide a quick enough dissolution rate, most desirably between about 1 minute and about 20 minutes, while providing an acceptable mucoadhesion level such that the film is not easily removable once it is placed in the oral cavity of the user.

Bioadhesion refers to the ability of certain synthetic and biological macromolecules and hydrocolloids to adhere to biological tissues. Mucoadhesion is the process of bonding of a synthetic or natural polymer(s) to the mucus membrane covering body tissue where wetting, adsorption and inter-penetration of the employed biopolymer chains occur [23]. Polymers containing hydroxyl, carboxyl, amide, and amine groups can establish hydrogen bonds and promote adhesion to the mucosa. Suitable mucoadhesive polymers include carboxymethyl cellulose, hydroxypropyl methyl cellulose, Carbopol® (carbomers), Noveon® (polycarbophils), polyacrylic acid, polyacrylates, copolymer of acrylic acid, chitosan, gelatin, hyaluronic acid, carrageenan, pectin and sodium alginate.

Other bioadhesive polymers of the present disclosure include, for example, gums like locust beam, xanthan, agarose, karaya, guar, and other polymers including but not limited to polyvinyl alcohol, polyvinyl pyrollidone, polyethylene glycol, Pluronic® (Poloxamers), tragacanth, and hyaluronic acid.

In some embodiments, the mucoadhesive polymer is a crosslinked polyacrylic acid polymer such as prop-2-enoic acid (i.e. Carbopol® 940). In some embodiments, the mucoadhesive polymer is at a concentration of about 1-10% w/v, e.g. about 3-5% w/v.

The film may be prepared by utilizing a selected casting or deposition method and a controlled drying process according to methods known in the art. For example, the film may be prepared through controlled drying processes, which include application of heat and/or radiation energy to the wet film matrix to form a visco-elastic structure, thereby controlling the uniformity of content of the film. Alternatively, the films may be extruded according to methods known in the art.

The film may further comprise one or more penetration enhancers (e.g. citral) and/or plasticizers (e.g. propylene glycol). Other suitable penetration enhancers include surfactants, fatty acids and derivatives, ethanol, chitosan, etc. For example, the penetration enhancer may be one or more of Sodium lauryl sulfate, Cetyl pyridinium chloride, Poloxamer, Brij, Span, Myrj, Tween, Oleic acid, Caprylic acid, Lauric acid, Lyso phosphatidyl choline, Phosphatidyl choline and Terpenes (such as eucalyptus). Other suitable plasticizers include glycerol, polyethylene glycols (PEG), castor oil, dibutyl phthalate, and sorbitol.

The compositions and films of the present disclosure may also contain other components such as, but not limited to, additives, adjuvants, buffers, tonicity agents, and preservatives. In any of the compositions of this disclosure, the mixtures are preferably formulated at about pH 5 to about pH 8. This pH range may be achieved by the addition of buffers to the composition. It should be appreciated that the compositions of the present disclosure may be buffered by any common buffer system such as phosphate, borate, acetate, citrate, carbonate and borate-polyol complexes, with the pH and osmolality adjusted in accordance with well-known techniques to proper physiological values. The micellar compositions of the present disclosure are stable in buffered aqueous solution. That is, there is no adverse interaction between the buffer and any other component that would cause the compositions to be unstable.

An additive such as a sugar, a glycerol, and other sugar alcohols, can be included in the compositions of the present disclosure. Pharmaceutical additives can be added to increase the efficacy or potency of other ingredients in the composition. For example, a pharmaceutical additive can be added to a composition of the present disclosure to improve the stability of the bioactive agent, to adjust the osmolality of the composition, to adjust the viscosity of the composition, or for another reason, such as effecting drug delivery. Non-limiting examples of pharmaceutical additives of the present disclosure include sugars, such as, trehalose, mannose, D-galactose, and lactose.

In an embodiment, if a preservative is desired, the compositions may optionally be preserved with any well-known system such as benzyl alcohol with/without EDTA, benzalkonium chloride, chlorhexidine, Cosmocil® CQ, or Dowicil 200.

Embodiments of the disclosure also include method of preparing the inclusion complexes disclosed herein. Various suitable methods are known in the art. In an embodiment, the inclusion complex is prepared using a saturated or super-saturated drug solution.

Embodiments of the disclosure also include methods of preparing the micelle compositions disclosed herein. Various suitable methods are known in the art. In an embodiment, the present disclosure provides a method of preparing a mixed micelle composition that includes mixing the active agent and other ingredients in an organic solvent (e.g. methanol). The methanol may then be evaporated, e.g. using a rotary vacuum evaporator. The prepared dispersion may then be centrifuged and the residue lyophilized using a freeze dryer. Other suitable solvents that can be used in preparing the micelle compositions of the present disclosure include short-chain alcohols, for example, ethanol, n-propanol, isopropanol, and butanol, as well as, chloroform, acetone, methylene chloride, dimethyl dulfoxide, dimethyl formamide and propylene glycol.

The present disclosure also provides a method of treatment of a human or non-human animal subject by delivery of a substantially insoluble or sparingly soluble biologically active agent, said method comprising administering to said subject a film of the disclosure as hereinbefore defined. Administration of the films described herein provides for enhanced or improved permeation of the drug across mucosal tissue.

The compositions and dosage forms of the disclosure may be useful for the treatment of any disease or disorder that the included active agent is useful for treating. For example, if simvastatin is used, the composition or dosage form may be useful for the treatment of hypercholesterolemia or dyslipidemia. In an embodiment, the film of the disclosure is applied topically to any mucosal tissue, e.g. to the buccal, palatal, gingival, lingual, sublingual or cheek mucosa of the buccal cavity.

A patient or subject to be treated by any of the compositions or methods of the present disclosure can mean either a human or a non-human animal including, but not limited to, dogs, horses, cats, rabbits, gerbils, hamsters, rodents, birds, aquatic mammals, cattle, pigs, camelids, and other zoological animals.

In some embodiments, the active agent (e.g. simvastatin) is administered to the subject in a therapeutically effective amount. By a "therapeutically effective amount" is meant a sufficient amount of active agent to treat the disease or disorder at a reasonable benefit/risk ratio applicable to any medical treatment. It will be understood that the total daily usage of the compositions of the present invention will be decided by the attending physician within the scope of sound medical judgment. The specific therapeutically effective dose level for any particular subject will depend upon a variety of factors including the disorder being treated and the severity of the disorder; activity of the specific compound employed; the specific composition employed, the age, body weight, general health, sex and diet of the subject; the time of administration, route of administration, and rate of excretion of the specific compound employed; the duration of the treatment; drugs used in combination or coincidental with the specific active agent employed; and like factors well known in the medical arts. For example, it is well within the skill of the art to start doses of the compound at levels or frequencies lower than those required to achieve the desired therapeutic effect and to gradually increase the dosage or frequency until the desired effect is achieved. However, the daily dosage of the active agent may be varied over a wide range from 0.01 to 1,000 mg per adult per day. In particular, the compositions contain 0.01, 0.05, 0.1, 0.5, 1.0, 2.5, 5.0, 10.0, 15.0, 25.0, 50.0, 100, 250 and 500 mg of the active ingredient for the symptomatic adjustment of the dosage to the subject to be treated. A medicament typically contains from about 0.01 mg to about 500 mg of the active ingredient, in particular from 1 mg to about 100 mg of the active ingredient. An effective amount of the drug is ordinarily supplied at a dosage level from 0.0002 mg/kg to about 20 mg/kg of body weight per day, especially from about 0.001 mg/kg to 7 mg/kg of body weight per day.

The active agent may be combined with pharmaceutically acceptable excipients. "Pharmaceutically" or "pharmaceutically acceptable" refer to molecular entities and compositions that do not produce an adverse, allergic or other untoward reaction when administered to a mammal, especially a human, as appropriate. A pharmaceutically acceptable carrier or excipient refers to a non-toxic solid, semi-solid or liquid filler, diluent, encapsulating material or formulation auxiliary of any type.

Before exemplary embodiments of the present invention are described in greater detail, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, representative illustrative methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

The invention is further described by the following non-limiting examples which further illustrate the invention, and are not intended, nor should they be interpreted to, limit the scope of the invention.

EXAMPLE

Summary

Simvastatin (SMV), a hypocholesterolemic agent, suffers from very low bioavailability due to its poor aqueous solubility and extensive first-pass metabolism. Two SMV carrier systems namely; polymeric drug inclusion complex (IC) and mixed micelles (MM), were developed and loaded into mucoadhesive buccal films to enhance SMV bioavailability. The two carrier systems were characterized and their permeation across human oral epithelial cells (OEC) was studied. The effect of IC to MM ratio ($X_1$) and the mucoadhesive polymer concentration ($X_2$) on the cumulative percent of drug released, elongation percent and mucoadhesive strength, from the prepared mucoadhesive films, was optimized. Ex vivo permeation across bovine mucosal tissue was investigated. The permeation parameters, for the in vitro and ex vivo release data, were calculated. Complexation of SMV with hydroxypropyl beta-cyclodextrin (HP-β-CD) was superior to all other polymers as revealed by the equilibrium saturation solubility, stability constant, complexation efficiency and thermodynamic potential. SMV-HP-β-CD IC was utilized to develop a saturated polymeric drug solution. Both carrier systems showed enhanced permeation across OEC when compared to pure drug. $X_1$ and $X_2$ were significantly affecting the characteristics of the prepared films. The optimized mucoadhesive buccal film loaded with SMV IC and drug MM demonstrated superior ex vivo permeation when compared to the corresponding pure drug buccal film, and the permeation parameters confirmed this finding. In summary, mucoadhesive buccal films containing SMV IC and SMV MM can be used to improve drug bioavailability.

Materials and Methods

Simvastatin (SMV) was kindly supplied from the Saudi Arabian Japanese Pharmaceuticals Co. Ltd (SAJA) (Jeddah, KSA). Methanol, pluronic F127, hydroxypropyl beta-cyclodextrin (HP-β-CD), propylene glycol, citral, dialysis tubing cellulose membrane with an average flat width of 1.7 inch and molecular weight cut-off of 14,000, sodium deoxycholate, polyethylene glycol (PEG 4000 & 6000) were all supplied from Sigma-Aldrich Inc. (St. Louis, Mo., USA). Polyvinyl pyrrolidone (PVP) with a molecular weight of 44,000 (PVP K30) and 360,000 (PVP K90) were obtained from Spectrum Chemicals & Laboratory Products (New Brunswick, N.J., USA). Polyvinyl pyrrolidone vinyl alcohol (PVP VA64) was purchased from Shanghai Yuking Water Soluble Material Tech Co., Ltd. (Shanghai, China). Hydroxypropyl methylcellulose (HPMC), molecular weight of 86000, viscosity 4000 cp (2% solution) was procured from Acros Organics (New Jersey, USA). Soybean phosphatidylcholine was obtained from Lipoid GmbH (Ludwigshafen, Germany). Carbopol 940 was purchased from Acros Organics (Morris Plains, N.J.). Beta-cyclodextrin (β-CD) was a kind gift from Nihon Shokuhin Kako Co., Ltd. (Toyo, Japan). Mucin powder was supplied from Xian Kono Chem Co., Ltd (Xi'an, China). All other chemicals and solvents were of analytical grade.

Preparation and Characterization of SMV Binary System

Selection of the Polymer

Eight different hydrophilic polymers were studied for their effect in enhancing SMV aqueous solubility after development of drug-polymer binary systems. PEG 4000, PEG 6000, PVP K30, PVP K 90, pluronic F127 and PVP VA64 were used to prepare solid dispersions in a drug to polymer ratios of 1:1, 1:2, and 1:4 (w/w). Drug inclusion complexes were also prepared utilizing β-CD and HP-β-CD in a drug to polymer molar ratios of 1:1 and 1:2. Kneading method was the technique utilized to develop the binary systems. Briefly, a specified weight of SMV was thoroughly mixed with the calculated amount of the studied polymer in a porcelain mortar and a diluted hydro-alcoholic solution was added dropwise with continuos mixing until slurries were formed. The prepared slurries were then kept in an oven at 40° C. until dried mixtures were obtained. Dried drug-polymer binary systems were finally grounded to fine powders, sieved and stored in a desiccator for further analysis.

Equilibrium Saturation Solubility Study

Excess amount of either pure SMV or the prepared binary systems was added to 10 mL distilled water in a screw cap glass vial. The prepared vials were placed in a thermostatically controlled shaking water bath, (Model 1031; GLF Corp; Burgwedel, Germany), at 25±0.5° C. for 72 hrs. Aliquots were withdrawn, filtered and assayed for drug content spectrophotometrically, using Jenway 6715 (Stone, UK), at 239 nm after 48 and 72 hrs., respectively to ensure complete drug solubility. Each experiment was performed in triplicate.

Phase Solubility Study

Based on the equilibrium saturation solubility study HP β-CD was selected, as this polymer enhanced the solubility of SMV significantly. The phase solubility study was carried out, according to Higuchi and Connors method [25], to investigate the type of interaction between SMV and HP β-CD. An excess amount of SMV was added into glass vials containing 10 mL of aqueous HP β-CD solution (2-20 mM). The vials were kept in a shaking water bath at a constant temperature for 72 hrs. Samples (n=3) from each vial were removed, filtered, and analyzed for SMV content spectrophotometrically at 239 nm. Phase-solubility plot was constructed and the stability constant (Ks) was calculated using the following equations:

$$\text{Stability Constant } (Ks) = \frac{\text{Slope}}{S_o(1 - \text{Slope})} \quad (1)$$

Where, $S_o$ is the solubility of SMV in the absence of HP β-CD (obtained from the intercept of phase solubility plot).

The complexation efficacy (CE), which gives information about the studied polymer solubilizing efficiency for SMV, was also calculated according to the following equation $$\text{Complexation Efficacy } (CE) = \frac{\text{Slope}}{1 - \text{Slope}} \quad (2)$$

The energy for transfer of SMV from pure water to aqueous solution of HP β-CD was calculated as Gibbs free energy ($\Delta G°_{tr}$). It refers to the thermodynamic potential that is minimized when a system reaches chemical equilibrium from an initial state to a final state at constant pressure and temperature. It was estimated applying the following equation:

$$\text{Gibbs free energy} (\Delta G° tr) = -2.303 \ RT \ \text{Log}\left(\frac{Sc}{S_o}\right) \quad (3)$$

where, (Sc/So) is the ratio of the molar drug solubility in aqueous solution of HP β-CD to that of pure water. R is the gas rate constant (8.314 J/° C.). T is the temperature in Kelvin at which the study was conducted.

Development of Saturated Polymeric SMV Solution ($1^{ST}$ Carrier System)

Preliminary Screening

To prepare a saturated HP β-CD drug solution, different polymeric solutions containing 20, 30, 40, and 50 mM of HP β-CD were prepared by dissolving the calculated amount of the polymer in 50% (v/v) hydro-alcoholic solution. Known excess of SMV was gradually added to each solution over a magnetic stirrer. The prepared solutions were left stirring overnight at 40° C. to ensure complete evaporation of methanol. Supernatants were decanted, filtered and assayed for SMV content spectrophotometrically at 239 nm.

Preparation of SMV-HP β-CD Inclusion Complex Saturated Solution

Based on the preliminary screening step, a saturated HP β-CD solution of 40 mM polymer was prepared in 50% hydro-alcoholic solution over a magnetic stirrer and known weight of SMV was subsequently added under a continuous stirring. The resulting polymeric drug solution was kept stirring overnight at 40° C. Finally, the supernatant was separated and filtered.

Physicochemical Characterization

Differential scanning calorimetry (DSC): The DSC thermograms of pure SMV, HP (3-CD, SMV-HP β-CD physical mixture and freeze-dried SMV-HP β-CD inclusion complex were investigated using the DSC apparatus of Shimadzu DSC TA-50 ESI (Tokyo, Japan). An aluminum crucible containing 5 mg of the studied sample was investigated under a dynamic N2 atmosphere at a heat flow rate of 10° C./min in a temperature range of 20–300° C.

Fourier transform infrared spectroscopy (FTIR): The FTIR spectra of the same samples used in the DSC study were recorded between 4000-400 $cm^{-1}$ using Nicolet iS10, Thermo Fisher Scientific (Waltham, Mass.).

X-ray powder diffraction (XRPD): To evaluate the crystallinity of pure SMV and freeze-dried SMV-HP β-CD inclusion complex, XRPD study was conducted. The diffraction patterns of both samples were recorded using a D/max 2500, Rigaku, powder X-ray diffractometer (Tokyo, Japan) at a scan speed of 0.5°/min.

Development of SMV-Mixed Micelles ($2^{nd}$ Carrier System)

The SMV loaded mixed micellar system was prepared as previously reported using phosphatidylcholine (PC) and sodium deoxycholate (SDC) in a ratio of (1:0.8) with a total PC/SDC of 54 mg/mL [26]. The calculated amounts of PC, SDC and SMV were dissolved in the least quantity of methanol. The organic solvent (methanol) was evaporated in a rotary evaporator at steady water bath temperature of 40° C. under a vacuum pressure using Buchi Rotavapor® R-200 Buchi labortechink AG, CH-9230 (Flawil, Switzerland). The dried thin layer obtained was then rehydrated with distilled water and kept shaking in the rotavapor for 30 minutes and finally dispersed for 15 minutes using ultrasonicator of Sonics Vibra cell, VCX 750; Sonics & Materials, Inc. (Newtown, Conn., USA). The obtained medicated mixed micelles were subjected to centrifugation at 15000 rpm for 5 min at 4° C. using (Sigma Laboratory centrifuge, 3K30, Ostrode, Germany) in order to separate the unloaded drug. The supernatant containing the medicated micellar system was kept in the refrigerator at 4° C. until further analysis.

Characterization of the SMV-Mixed Micelles

Drug Content and Encapsulation Efficiency

Known volume of the prepared micellar solution was diluted, in a ratio of 1:10 v/v, with pure ethanol and SMV content was determined spectrophotometrically at 239 nm. The encapsulation efficiency (EE) was calculated according to the following equation:

$$EE = \frac{\text{Calculated amount of } SMV \text{ in the micellar system}}{\text{Amount of } SMV \text{ intially added}} \times 100 \qquad (4)$$

Morphological Study

Surface morphology of the prepared micellar system was observed using transmission electron microscope (TEM) Model JEM-1230, JOEL (Tokyo, Japan). Briefly, a few drops of the prepared micellar solution were mounted on a carbon coated grid and left for 5 min to allow for better adsorption on the carbon film. Excess liquid was removed by means of a filter paper. Finally, a few drops of 1% phosphotungstic acid was added and the sample was examined.

Particle Size Distribution and Zeta Potential Measurement

Determination of particle size, zeta potential and polydispersity index for the prepared micellar system were performed using Malvern Zetasizer Nano ZS, Malvern Instruments (Malvern, UK).

Permeability Study

This section aimed to investigate the ability of both carrier systems to penetrate the cell membrane of the oral cell tissue. Human oral epithelial cells (OEC), Applied Biological Materials Inc. (Richmond, BC, Canada) were cultured and seeded ($1\times10^6$ viable cells) on T25 flasks. The culture medium was replaced daily, while the cells were examined for their electrical resistance and apparent permeability coefficient until suitable for the experiment. The OEC were divided into three groups. The first group was exposed to 0.1 mg/mL SMV in the form of inclusion complex in dimethyl sulfoxide (DMSO). The second group was treated with the same drug concentration in the form of mixed micelles. The third group was subjected to the same concentration of pure SMV in DMSO. Blank OEC containing only the culture medium without drug was used as a reference. The experiment was conducted in triplicate. The OEC were incubated, collected at predetermined specified times and washed twice with ice-cold phosphate buffer saline. The collected cell pellets were suspended in 1 mL hypotonic saline solution, subjected to three repeated cycles of freezing and thawing and then exposed to ultrasonic homogenization for 10 minutes to ensure complete rupture of the cells. Finally, cell lysates were subjected to centrifugation at 15,000×g for 60 minutes at 4° C. using 3K30 sigma laboratory centrifuge (Osterode am Harz, Germany). The concentration of SMV in the supernatant was calculated using high performance liquid chromatography (HPLC) method [27,28]. Agilent 1200 HPLC system of Agilent Technologies, Palo Alto (CA, USA) equipped with a UV diode array detector was used. The chromatographic analysis was performed using methanol-0.05 M potassium dihydrogen orthophosphate (pH 5) (80/20 v/v) as a mobile phase. The flow rate was adjusted at 1.2 mL/min and the absorbance was detected at 239 nm. SMV retention time was detected at 9.7 mL/min. Drug standards containing known weight of SMV in the OEC were prepared, treated as mentioned above and assayed for drug content before determination of the unknown SMV concentrations in the tested samples.

Development of SMV Mucoadhesive Buccal Films

Experimental Design

A response surface, 3-level factorial design, was used as a statistical tool to explore the effect of mixed micelles to inclusion complex ratio ($X_1$) and the carbopol percent ($X_2$) on the cumulative percent of drug release ($Y_1$), elongation percent ($Y_2$) and mucoadhesive strength ($Y_3$) from SMV-mucoadhesive buccal films. StatGraphics Centurion XV version 15.2.05 software, StatPoint Technologies, Inc. (Warrenton, Va., USA) was used to generate formulations and to statistically analyze the obtained results. A ratio of 1:2-2:1 and a concentration of 0-10% were used for $X_1$ and $X_2$, respectively. The goal was to maximize $Y_1$—$Y_3$. A total of 9 experimental runs were obtained and their compositions are shown in Table 1.

TABLE 1

Experimental runs and the observed values for simvastatin mucoadhesive buccal films obtained from the three-level factorial design.

| Run | $X_1$ (Ratio) | $X_2$ (%) | $Y_1$ (%) Observed | $Y_1$ (%) Predicted | $Y_2$ (%) Observed | $Y_2$ (%) Predicted | $Y_3$ (Newton) Observed | $Y_3$ (Newton) Predicted |
|---|---|---|---|---|---|---|---|---|
| F1 | 1:2 | 10 | 64.91 | 64.91 | 20.0 | 17.22 | 804.0 | 793.27 |
| F2 | 1:1 | 10 | 72.7 | 72.7 | 25.0 | 31.38 | 715.0 | 771.44 |
| F3 | 1:1 | 0 | 91.4 | 91.4 | 150.0 | 126.38 | 218.0 | 191.77 |
| F4 | 2:1 | 5 | 85.8 | 85.8 | 100.0 | 92.22 | 583.0 | 633.11 |
| F5 | 2:1 | 0 | 101.2 | 101.2 | 150.0 | 161.38 | 220.0 | 215.61 |
| F6 | 1:2 | 0 | 86.7 | 86.7 | 80.0 | 92.22 | 250.0 | 280.61 |
| F7 | 2:1 | 10 | 84.9 | 84.9 | 50.0 | 46.38 | 908.0 | 862.27 |
| F8 | 1:1 | 5 | 81.03 | 81.03 | 50.0 | 67.22 | 606.0 | 575.77 |
| F9 | 1:2 | 5 | 75.4 | 75.4 | 52.5 | 43.05 | 651.0 | 631.11 |

Abbreviations:
$X_1$, mixed micelle to inclusion complex ratio; $X_2$, percent of carbopol; $Y_1$, cumulative percent of drug released; $Y_2$, elongation percent; $Y_3$, mucoadhesive strength.

Preparation of the SMV-Mucoadhesive Buccal Film

Different SMV mucoadhesive buccal films were prepared using different ratios of $X_1$ and various concentrations of $X_2$ utilizing the solvent casting technique. Briefly, known volumes of the prepared mixed micelles and polymeric drug inclusion complex were mixed and completed to 50 mL with distilled water. The penetration enhancer (citral) and the plasticizer (propylene glycol) were subsequently added to the above mixture, in a concentration of 2% each, and the mixture was thoroughly mixed over a magnetic stirrer. HPMC (1% w/v), as a film-forming agent, and the specified concentration of carbopol 940, as a mucoadhesive polymer, were eventually added. The obtained mixtures were left overnight in a refrigerator to allow complete swelling of the polymers and formation of a clear solution. The prepared SMV polymeric solutions were poured into 9 cm diameter glass petri dishes, about 64 $cm^2$ dish area, and kept in an oven at 40° C. until complete drying. A drug load equivalent to 688 μg for each buccal film that has diameter of 1.5 cm (1.76 cm² area) was considered. Finally, the prepared films were stored in a sealed desiccator until further characterization.

Characterization of SMV Buccal Films

Content Uniformity

To ensure good distribution of SMV in the prepared mucoadhesive buccal films, the content uniformity was evaluated. Three films, of 1.76 cm² area, from each formulation were immersed into 50 mL hydro-alcoholic solutions (50:50) in a 100 mL glass bottles that were incubated in a shaking water bath at 25° C. for 48 h. Aliquots from each bottles were withdrawn, filtered using 0.45 μm syringe filter and analyzed for SMV content using UV-Vis spectrophotometer at λ max of 238 nm. The average reading of three films was considered and compared to the theoretical drug load.

Thickness

Digital micrometer of Mitutoyo Co. (Kawasaki, Japan) was utilized to determine the average thickness of ten individual readings from each formulation.

Percent Elongation

To measure the stretch of a film strip sample when a stress is applied, strain or the elongation percent is measured [29]. An elongation testing apparatus that has been designed in our laboratory was used for the measurement as previously published in our work [30]. A rectangular film strips (1×4 cm), from each formulation, were placed between two jaws separated by 2 cm. The upper jaw is fixed in position while the lower one is freely moving and is attached to a definite weight. The change in the strip length after a time of five minutes was measured. The experiment was done in triplicate for each film. The percent elongation was calculated utilizing the following equation:

$$\text{Elongation (\%)} = \frac{\text{The final length of the film} - \text{Initial length of the film}}{\text{Initial length of the film}} \times 100 \quad (5)$$

Evaluation of the Mucoadhesive Strength

Mucoadhesion is a characteristic of a dosage form that can interact with mucosal membranes; especially with their mucin component [31]. To evaluate this property for buccal films, the mucoadhesive strength is utilized to measure the force needed to detach the film from the buccal cavity [32]. In this study, two techniques have been utilized to evaluate the mucoadhesive strength of the prepared buccal films namely, the tensile strength method [32] and the mucin particle method [33]. The aim was to compare and validate results obtained from both methods. The first method is based on measuring the interaction between the film and buccal tissue physically, while the second is based on evaluating the change in zeta potentials produced upon interaction of the prepared film with mucin powder suspension. Results obtained for the mucoadhesive strength using the tensile strength apparatus method were used in the experimental design; while the other results for the mucin particle method were used for comparison and validation purposes only.

Evaluation of Mucoadhesive Strength Using Tensile Strength

In this experiment, the force required to break the interaction between the prepared film and the buccal mucosal tissue was used to assess the mucoadhesive strength [31]. Cow buccal mucosal tissue, obtained from local slaughterhouse, was used as a model to evaluate the mucoadhesive properties for the prepared films using Shimadzu Tensile Strength Machine, EZ-SX with high-precision (±0.5%), Shimadzu Co. (Kyoto, Japan). Briefly, a buccal tissue of 2 cm² was fixed on a glass slide attached to the apparatus lower stage (stationary platform). Samples from each films of the same surface area were adhered to another glass slide, using two-sided adhesive tape, that was attached to the apparatus upper platform. The film was allowed to interact with the mucosal tissue by applying downward force for 2 minutes before running the experiment. The crosshead was then raised at a constant speed of 0.5 mm/min and the force required for complete detachment (break point) was recorded. Each experiment was repeated three times.

Evaluation of Mucoadhesive Strength Using Mucin Particle Method

A simple method that depends on measuring the zeta potential of a mucin powder suspension before and after incubation with a known weight of the studied films for 48 h was used [27,33,34]. Briefly, a mucin powder suspension was prepared by adding an excess amount of bovine mucin into a 100 mM acetate buffer solution and mixed overnight to ensure complete dispersion. The mixture was then centrifuged for 15 mins at 26,000 rpm at 4° C.; and the supernatant was separated [34]. A known weight (45 mg) from each film was dipped into a test tube filled with 3 mL of the prepared mucin suspension and the mixture kept in a shaking water bath for 48 h. Zeta potentials of the prepared mixture and the mucin powder suspension were finally measured using Malvern Zetasizer Nano ZS, Malvern Panalytical Ltd Instruments (Malvern, UK).

Results obtained for both methods (tensile strength and mucin particle method) were compared to validate the second method and authenticate a simple reliable method for determination of bioadhesiveness.

In Vitro Release Study

The release of SMV from the prepared medicated buccal films was investigated using an automated Franz diffusion cell apparatus of Hanson research, Microette Plus (Chatsworth, Calif., USA) over a period of 6 h. The apparatus is adapted with 1.76 cm² diffusion area and a receptor chamber of 7 mL volume. Synthetic cellulose membrane of Sigma-Aldrich Inc., molecular weight cut-off=14,000, was used as a diffusion membrane. Buffer solution of pH 6.2, to simulate the buccal saliva, containing 0.5% sodium lauryl sulphate was used as a diffusion medium. Buccal films of 1.76 cm² were placed in the receiver chamber above the diffusion membrane and the system was maintained in an occlusive condition. Aliquots were withdrawn automatically and analyzed by HPLC as previously described. Each buccal film formulation was studied in triplicate.

Experimental Design Statistical Analysis and Optimum Desirability

The statistical significance for the relationship between the independent ($X_1$ and $X_2$) and dependent variables ($Y_1$, $Y_2$ and $Y_3$) was identified after introduction of the obtained results into the response column of the Statgraphics Plus® software. Data was considered significant at p-value <0.05. The optimum desirability was estimated and the optimized formulation that achieves the study goal was proposed.

Preparation and Characterization of the Optimized SMV Buccal Film

The proposed optimized SMV loaded buccal mucoadhesive film formulation was prepared, characterized for the cumulative drug release ($Y_1$), elongation percent ($Y_2$) and mucoadhesive strength ($Y_3$) as previously mentioned. The obtained results (observed values) were compared to the predicted ones and the residual was calculated.

In Vitro Dissolution Time

The time needed for complete dissolution of the optimized buccal film was assessed according to the method previously published by Vila et al [21]. A small film strip (n=3) was added to 25 mL of ultrapure distilled water maintained at 37° C. in a 50-mL beaker that was kept under magnetic stirring with vortex formation. The elapsed time until the film strip was totally dissolved was recorded.

Ex Vivo Release Study

A fresh cow buccal mucosal tissue was used to evaluate SMV release from the optimized mucoadhesive buccal film formulation loaded with either the pure drug or the SMV carriers (mixed micelles and polymeric drug inclusion complex). Cow buccal mucosa, without any treatment, was freshly obtained from a local slaughterhouse immediately after the animal was killed and stored on ice until it was transferred to our laboratory. The study was conducted according to the same procedure described in the in vitro permeation section except that the cow buccal tissue was used to replace the artificial cellulose membrane.

Permeation Parameters of SMV Mucoadhesive Buccal Films Release Data

The in vitro and ex vivo permeation profiles of SMV from the prepared buccal films were constructed and the steady flux (Jss) was estimated from the slope of the gradient portion of the linear curve obtained by plotting the cumulative SMV permeated per unit area against time. SMV permeability coefficient (P) was calculated using the equation: $P=Jss/C_o$. Where $C_o$ is the initial SMV concentration in the donor compartment. SMV diffusion coefficient (D) was determined by representing the cumulative amount of drug permeated against the square root of time and applying the following equation: $D=(slope/C_o)^2 * \pi$.

Results and Discussion

SMV Binary Systems

SMV is considered a poorly water soluble drug [35]. The obtained results for the aqueous solubility of pure SMV, at 25° C., revealed an average solubility value of 10.692±0.0153 μg/mL as indicated in FIG. 1. Screening with certain polymers was performed to select the most suitable one that is capable of preparing a drug binary system of enhanced drug aqueous solubility. Kneading technique was employed to prepare drug-polymer binary systems. The equilibrium saturation solubility and phase solubility study have been performed to deduce the solubility efficiencies of the prepared binary systems.

Two types of binary systems, inclusion complex and solid dispersion, were investigated utilizing eight different hydrophilic polymers at different drug to polymer ratios. The solubility of SMV in these binary systems is illustrated in FIG. 1. Results of the equilibrium saturation solubility illustrated superiority of HP β-CD over all the studied polymers. An improvement in SMV aqueous solubility by more than 11 folds, when compared to the solubility of pure SMV, was obtained with HP β-CD at 1:2 drug to polymer ratio. This effect could be attributed to an efficient drug entrapment in the hydrophilic cyclodextrin cavity, enhanced wettability of SMV's particles, and to the change in the drug crystallinity from crystallin to amorphous state. This finding is in a good agreement with Zhang and his coworkers who studied the influence of HP β-CD complexation on the aqueous solubility and bioavailability of toltrazuril [36]. Parmar and his colleagues also reported similar finding for the effect of HP β-CD on lamotrigine [37]. They attributed the improvement of lamotrigine bioavailability and dissolution characteristics to the complete entrapment of the drug inside of the cyclodextrin cavity and to the change in drug crystallinity. Similar finding was also mentioned for the enhancement of aripiprazole dissolution after preparing a drug cyclodextrin binary systems [17].

Figure 2:
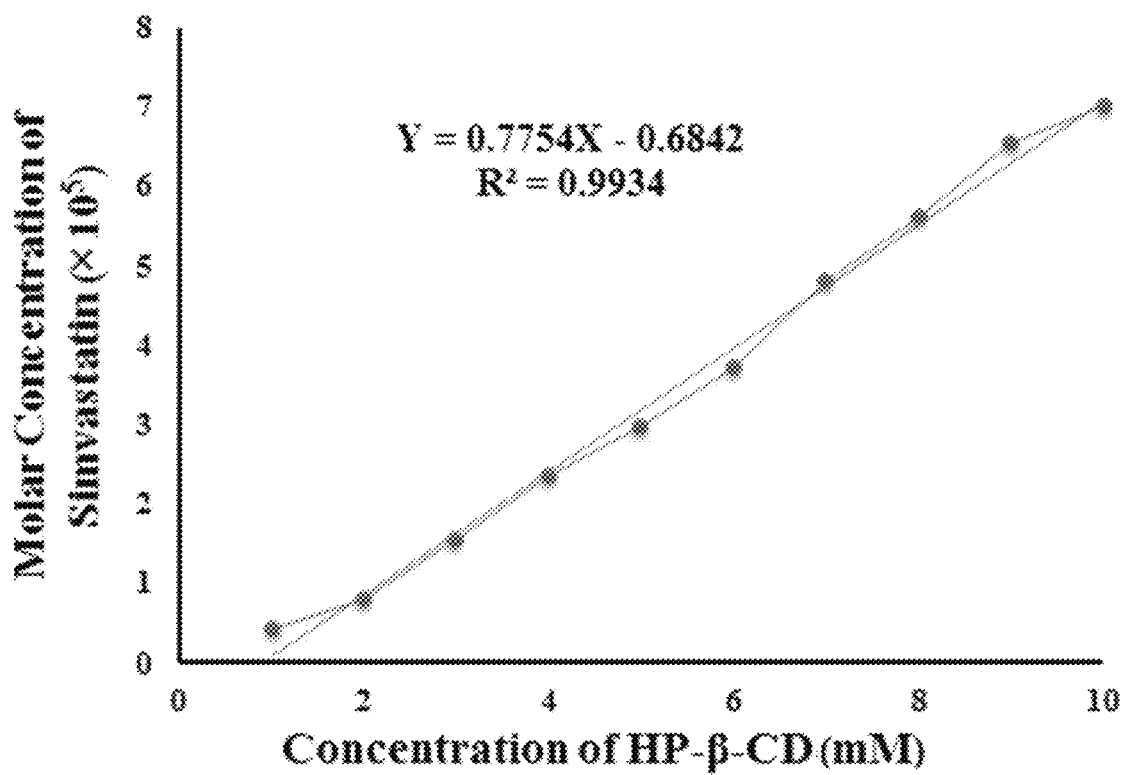
FIG. 2. Phase solubility study of simvastatin in aqueous solution of hydroxypropyl-beta-cyclodextrin.
Figure 3:
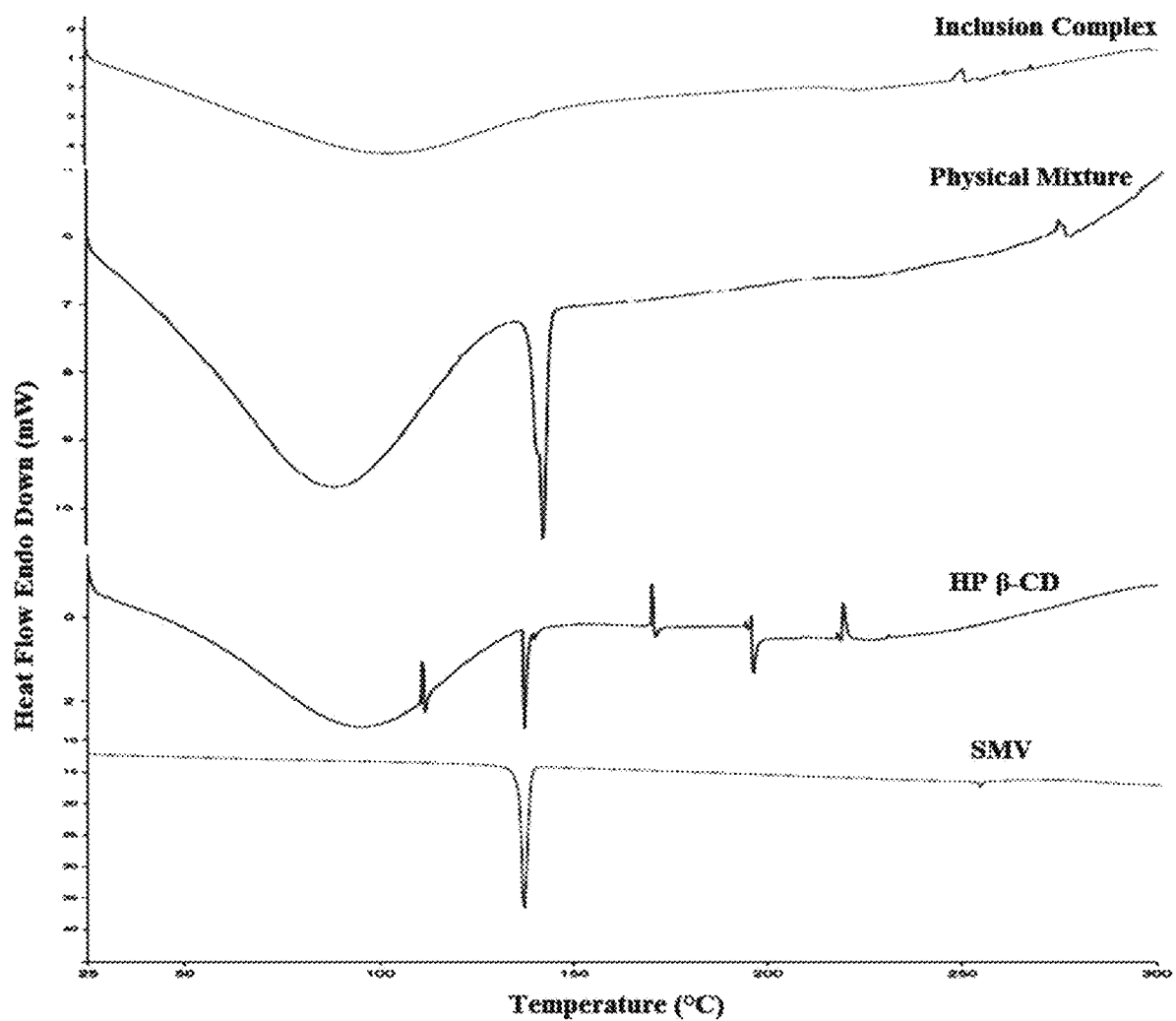
FIG. 3. Differential scanning calorimetry thermograms of pure SMV, HP β-CD, physical mixture and inclusion complex.
Figure 4:
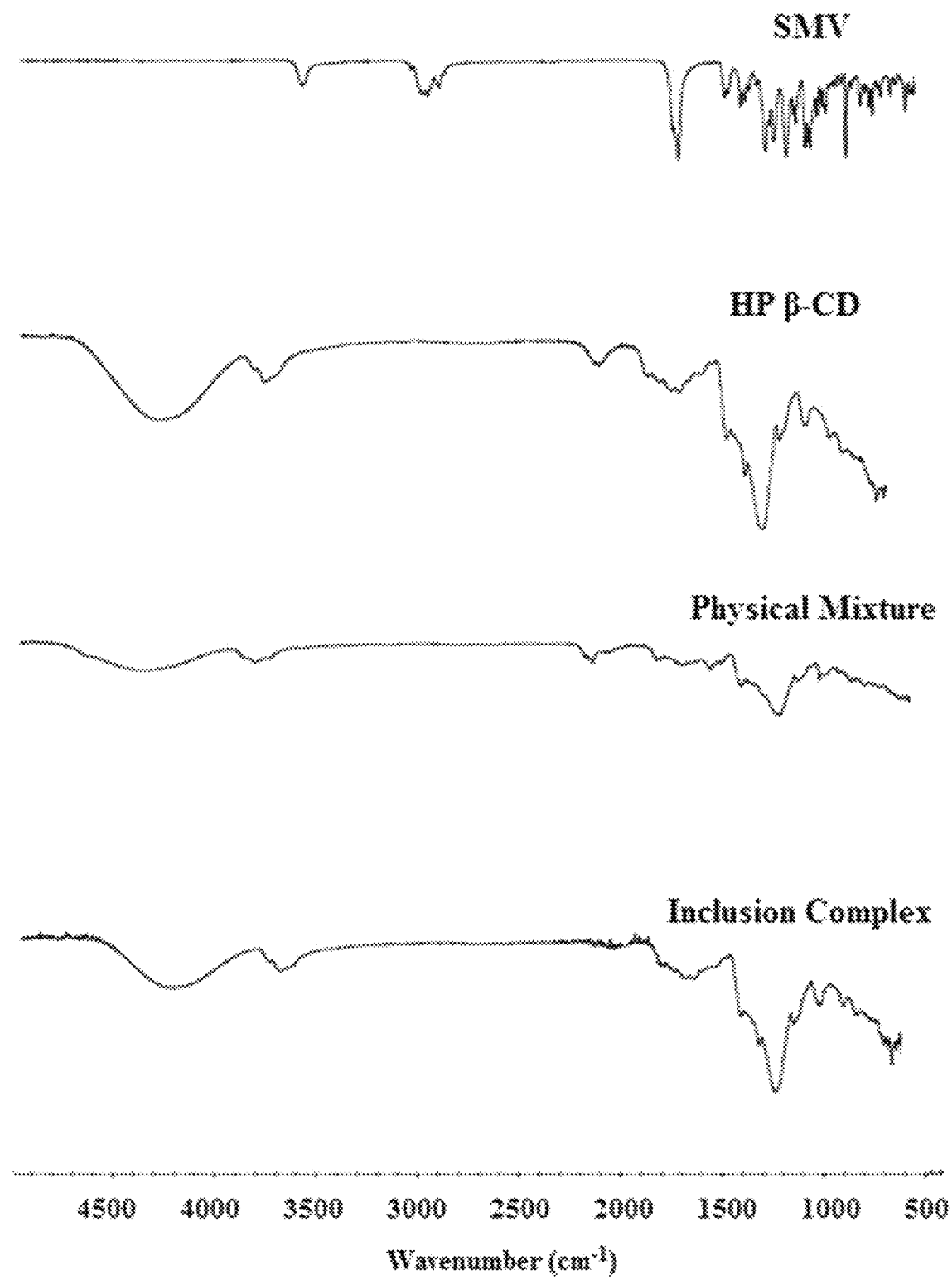
FIG. 4. Fourier transform infrared spectrum of pure SMV, HP β-CD, physical mixture and inclusion complex.
Figures 5A, 5B:
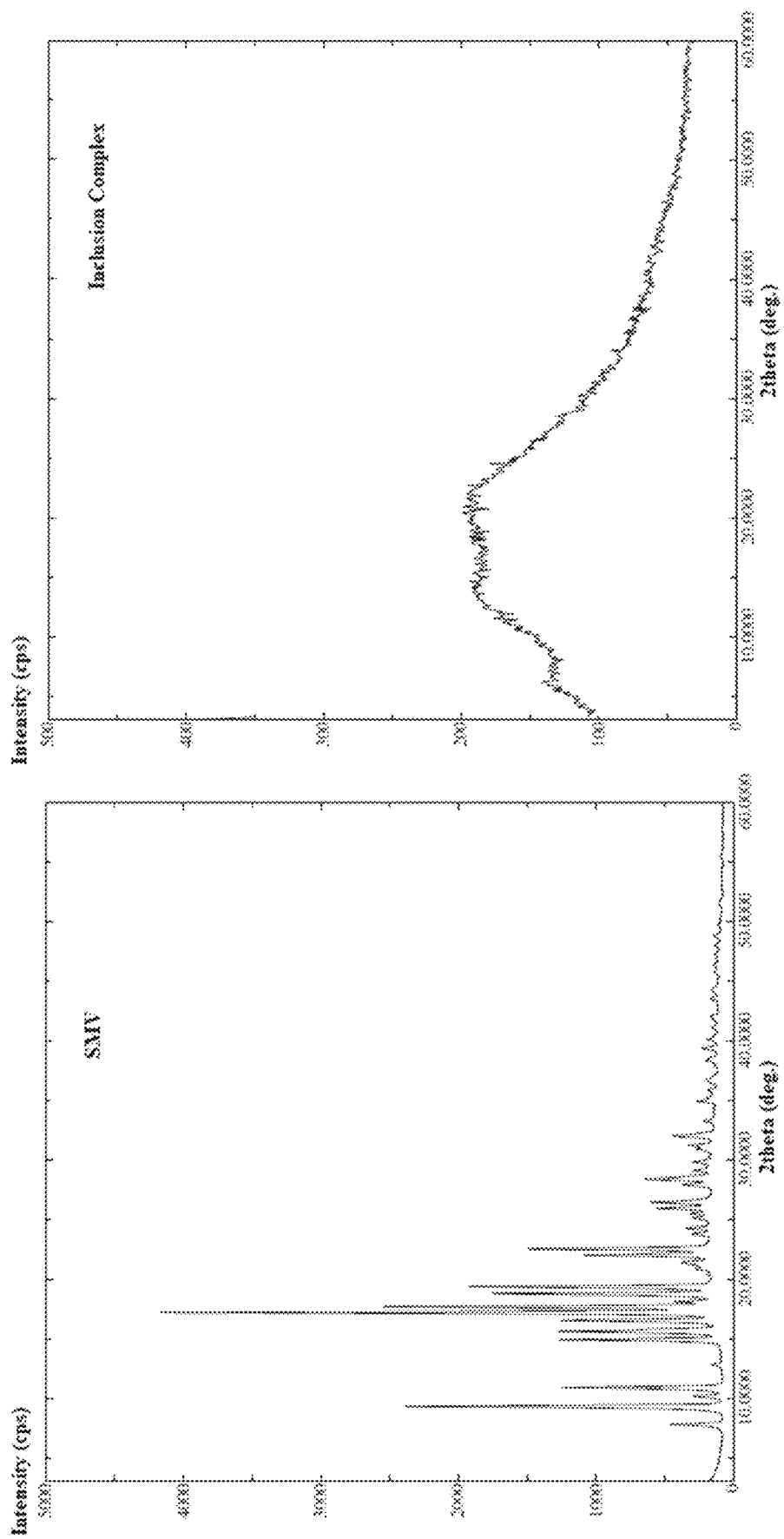
FIG. 5A-B. X-ray powder diffraction of (A) pure simvastatin and (B) inclusion complex.

A phase solubility study was performed to investigate the interaction of SMV with HP β-CD. Results obtained are graphically represented in FIG. 2. It was noticed that the solubility of SMV was improved upon increasing the molar concentration of HP β-CD. The equation that best describes the relationship was found to be; Y=0.7754 X−0.6842. The obtained regression coefficient ($R^2$) was 0.9934, which indicates an excellent correlation. The calculated stability constant (Ks) and the complexation efficacy ($C_E$) were found to be 0.3228 $M^{-1}$ and 3.4523, respectively. According to Higuchi and Connors classification [25], two types of complexation are most likely to occur; type A and type B. The former occurs when the solubility of the drug is increased upon increasing the polymer concentration. The latter is obtained when the solubility of the drug is increased with increasing the polymer concentration up to a certain limit followed by a plateau [10]. The former (type A) may be further classified into $A_L$ and $A_P$ types. When the drug solubility is increased upon increasing the concentration of the polymer and the complex formed is first order with respect to the polymer and first or higher order with respect to the drug, type $A_L$ is formed. If the complex obtained is first order with respect to the drug, but second or higher order with respect to the polymer, then $A_P$ type complexation is obtained. According to the data obtained, graphically illustrated in FIG. 2, an $A_L$ type of complexation between HP β-CD and SMV was formed since SMV solubility was increased upon increasing the concentration of the polymer and the complex formed was first order with respect to HP β-CD and first or higher order with respect to SMV. Our results are in a good agreement with Mura et al, who studied the solubilizing competency and complexation tendency of HP β-CD toward flufenamic acid in buccal cavity environment and reported an $A_L$ type of complexation [38]. The phase solubility study of acyclovir with HP β-CD showed the same outcome; a linear increase in the solubility of acyclovir was noticed upon increasing the HP β-CD concentration [39]. The interesting similarity of the phase solubility study results of HP β-CD with different drugs may be attributed to the capability of this polymer to incorporate the studied drug into the polymer cavity with an efficiency of complexation stability produced. Thus, HP β-CD could be considered as a polymer of choice for many poorly soluble drugs utilizing the inclusion complexation technique.

To evaluate the process of SMV solubilization in aqueous media of HP β-CD at different concentrations, Gibbs free energy)(ΔGtr°) was calculated to indicate whether the process is appropriate or not [10,40,41]. Results for Gibbs free energy of SMV in aqueous solution of HP β-CD at 25° C. indicated marked change in ΔGtr° from −1261.35 to −8214.49 (J/mol) when the HP β-CD molar concentration was increased from 2 to 20 mM. The obtained negative values indicated spontaneous thermodynamic reaction between SMV and HP β-CD molecules in the aqueous medium. Moreover, the decrease in the negativity of $\Delta G_{tr}°$ means that the system reactions become more favorable as the carrier concentration increased. This behavior could be attributed to the increase in van der Waals, electrostatic and hydrogen bonding upon increasing the cyclodextrin concentrations.

Development of Saturated Polymeric SMV Solution ($1^{ST}$ Carrier System)

Figure 6:
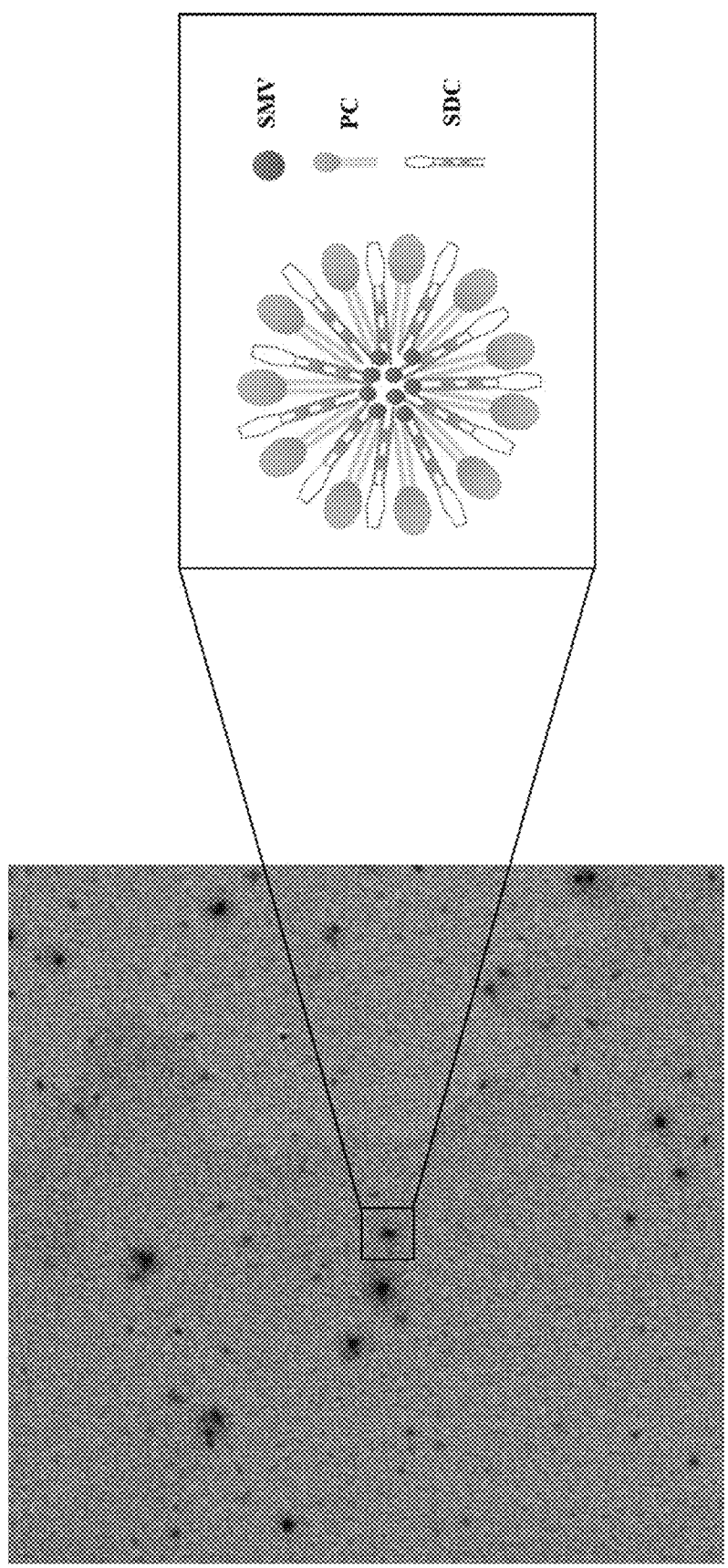
FIG. 6. The morphology of simvastatin mixed micelles formulation under TEM.

Cyclodextrins are a family of cyclic oligosaccharides that create a 3-dimensional toroid structure, providing a cavity that can accommodate hydrophobic molecules [42]. It has been reported that complexation with cyclodextrins is used to improve the solubility and enhance the bioavailability of varieties of active pharmaceutical agents such as lamotrigine [37], toltrazuril [36], aripiprazole [17], dexamethasone [43], niclosamide [44], clozapine [45], and others.

A saturated polymeric drug solution was prepared utilizing the inclusion complex of SMV and HP β-CD at 40 mM polymer solution. Selection of this concentration of the HP β-CD solution was based on stability of the complex and content uniformity. Solubility of SMV in this polymeric solution was increased by more than 114 folds (1229.73 μg/mL) when compared to the aqueous solubility of pure SMV (10.69 μg/mL). This behavior is attributed to efficient and full entrapment of the drug molecules in the polymer cavity. This finding was also noticed, in our previously published work, with glimepiride in aqueous polymeric solution of polyvinyl pyrrolidones and we attributed this effect to the improvement in drug wettability [46].

Physicochemical Characterization of SMV-HP β-CD IC

The physiochemical properties of pure SMV and HP β-CD were studied using DSC, FTIR and XRPD in order to assess the characteristics of both components in their physical mixture and the prepared freeze-dried inclusion complex.

Differential scanning calorimetry (DSC) is a validated tool for studying thermodynamic changes and the interactions that occur between tested components [47]. The DSC thermographs of pure SMV, HP β-CD, their physical mixture and the freeze-dried inclusion complex are illustrated in FIG. 3. The thermogram of pure SMV revealed a sharp endothermic peak at 141.35° C. indicating the crystallinity of the drug, while the thermogram of HP β-CD showed a short broad endothermic peak between 50-110° C. The physical mixture of the two components, SMV and HP β-CD, illustrated distinctive peaks corresponding to each component which indicates lack of interference and absence of any possible interaction upon physical mixing of the two components. The thermogram of the freeze-dried inclusion complex revealed absence of the drug melting endothermic peak and the presence of the HP β-CD's broad peak. This finding confirms drug polymer complexation and inclusion of the drug inside the HP β-CD cavity. Choi et al, reported similar finding for paclitaxel during development of drug-(2,6-di-O-methyl)-b-cyclodextrin inclusion complex. They mentioned absence of the drug endothermic peak and attributed this behavior to the molecular encapsulation of paclitaxel within the (2,6-di-O-methyl)-b-cyclodextrin cavity [48].

FTIR spectroscopy is another physicochemical characterization technique that measures how much light from a beam containing many frequencies is absorbed by the sample. A spectrum of the signal at a series of discrete wavelengths is obtained and used as a fingerprint of the sample. FTIR has been widely used to assess the characteristics of cyclodextrins [49]. Change in the intensity of the stretching vibration, absence, or shift in bands locations can be correlated with complexation [41,47]. The FTIR spectra of pure SMV, HP β-CD, their physical mixture, and the freeze-dried inclusion complex are illustrated in FIG. 4. Pure SMV showed a distinct peak at 3545 $cm^{-1}$ corresponding to the hydroxyl (O—H) stretching vibration. The alkene (C—H) stretching vibrations were observed at 3010 $cm^{-1}$ and 2810 $cm^{-1}$. Another characteristic peak for the lactone functional group (—C—O) was observed at 1700 $cm^{-1}$. SMV carbonyl (—C═O) groups were detected at 1164 $cm^{-1}$ and 1066 $cm^{-1}$ [27,50]. The FTIR spectra of HP β-CD demonstrated a prominent band at 3600 $cm^{-1}$ due to hydroxyl (O—H) group stretching vibration. Bands in the range of 1384-1460 $cm^{-1}$ corresponding to $CH_2$ and $CH_3$ bending vibrations were observed. Other bands at 1142 $cm^{-1}$ and 972 $cm^{-1}$ for (C—H) and (C—O) stretching vibrations, respectively were also noticed [51]. The spectra of the physical mixture showed a slight overlapping and a small reduction in the intensity of HP β-CD peaks, which indicate that partial complexation might have occurred through weak interaction. In contrast, SMV vibrational peaks were mostly absent in the spectra of the inclusion complex. This finding indicates that the drug (O—H) and (—C—O) groups interacted with the HP β-CD side chain. Moreover, the two distinct peaks of HP β-CD namely (O—H) and (C—H, C—O) stretching vibrations did not shift and still located at their locations during complex formation which confirmed the stability of the inclusion complex formed.

X-ray powder diffraction (XRPD) is a technique used to assess the crystallinity of a pure drug or its physically modified (inclusion complex) components in the solid state [49]. It has been used as another supporting tool that identifies the formation of drug inclusion complex. The change in the intensity of diffraction peaks or shifting in their locations might confirm complex formation [47]. The freeze-dried inclusion complex was utilized in this type of analysis. XRPD of pure SMV illustrated several intense diffraction peaks of the crystalline drug structure as shown in FIG. 5A-B. XRPD pattern of the prepared drug inclusion complex revealed a flat diffraction pattern with many peaks of low intensity, corresponding to an amorphous substance.

Based on the results for DCS, FTIR and XRPD, SMV might be hosted as a guest in the HP β-CD cavity with the drug crystallinity changed into amorphous form. This finding confirms inclusion complex formation and resulted in enhancement of the drug aqueous solubility.

Development and Characterization of SMV-Mixed Micelles ($2^{nd}$ Carrier System)

SDC and PC are amphiphilic molecules that have the ability of self-assembly in aqueous solution just above the CMC. In this study, both substances were used to develop SMV loaded mixed micelles as a drug nanocarrier system. Selection of both components was based on their tolerability and safety [26]. Drug loaded SDC/PC mixed micelles have been reported to improve solubility of poorly soluble drugs such as curcumin [52], Cucurbitacin B [26] and amphotericin B [53]. Although SDC alone could be used to form micelles and to solubilize insoluble drugs, the solubilization ability of the micelles prepared using this component alone is far lower than that of bile salt/PC mixed micelles [52]. During mixed micelles formation the hydrophobic part of bile salt, SDC, interacts with the PC acyl chain to form the micelle hydrophobic core while the hydrophilic shell is in direct contact with water. This effect, to a certain extent, is dependent on the concentration of the bile salts as previously suggested by Mazer et al [54]. Development of SMV loaded SDC/PC mixed micelles was achieved using the solvent evaporation technique, followed by centrifugation and separation of the drug loaded mixed micelles particles.

The prepared mixed micelles system increased the aqueous solubility of SMV by more than 430 folds, i.e. from 10.69 μg/mL to 4611.89 μg/mL. The average EE (%) was calculated as 54±0.88%. The average zeta potential value for the prepared mixed micelles was −30.81±2.12 mV. The negativity of the zeta potential is mainly attributed to the presence of the anionic surfactant, SDC, which surrounds the micelles, and attributed to formation of stable particles. It has been previously reported that when surface electric charge is close to the critical value (±30 mV), mutual repulsion between particles occur, which keep the system stable [55]. The mean particle size of the prepared mixed micelles was found to be 16.48±1.516 nm; which is in the nano-sized range (1 to 100 nanometers). The obtained value for PDI was 0.2157±0.081, which indicates high homogeneity of the prepared particles. Morphological study of the mixed micelles formulation revealed formation of spherical nanoparticles without aggregation as illustrated in FIG. 6. It has been suggested that mixed micelles illustrate spherical shaped nanoparticles with the phospholipid bilayer in the center and bile salts surrounding the perimeter of micelles, which is referred to as "mixed disk model" formulation [56]. It is expected that our formulation exhibits the same behavior; the soybean phosphatidylcholine molecules are in the center, with sodium deoxycholate molecules surrounding the perimeter, while SMV is dissolved in the mixed micelles core as graphically illustrated in FIG. 6.

Permeability Study

Figure 7:
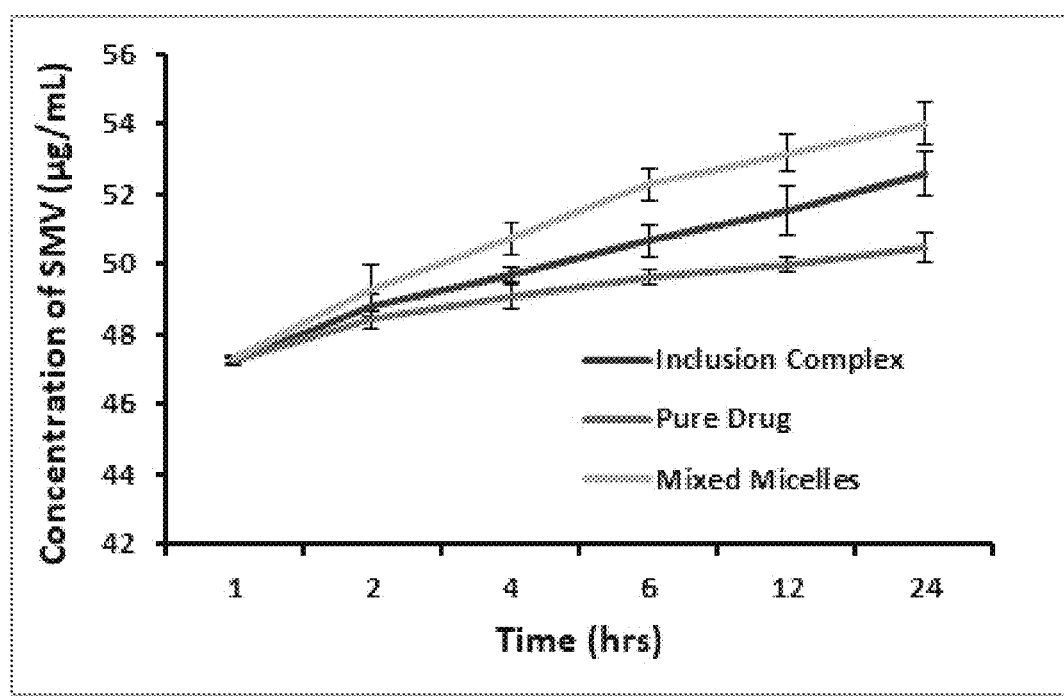
FIG. 7. Simvastatin intracellular permeation across human oral epithelial cells following treatment with different drug formulations.

The ability of the developed SMV carriers to permeate across the buccal mucosa was studied and compared to pure drug. FIG. 7 illustrates the intracellular drug concentration after exposure of the human oral epithelial cells (OEC) to 0.1 mg/mL different formulations of SMV. Based on the Biopharmaceutics Classification System, SMV is a class-II compound that is characterized by a poor aqueous solubility and an adequate permeability through biological membranes [57]. Acceptable drug permeation was noticed from the pure drug. The inclusion complex and the mixed micelles formulations resulted in enhanced SMV permeation with the mixed micelles formulation as the best. The superiority in the drug permeation from mixed micelles formulation could be attributed to the smaller size and the nature of the components (Sodium deoxycholate and soybean phosphatidylcholine) which facilitate the SMV transport across the cell membrane. Previous studies have also indicated enhancement in the rate of vinpocetine permeation across the buccal oral epithelial cells from a drug complex, in the form of solid dispersion with polyvinyl pyrrolidone vinyl acetate, when compared to pure vinpocetine solution [10].

Development of SMV Mucoadhesive Buccal Films

Different SMV loaded buccal films were prepared using different ratios of mixed micelles to inclusion complex ratio ($X_1$) and various percentage of carbopol ($X_2$) utilizing the solvent casting technique. HPMC was used as a film-forming substance while citral and propylene glycol were used as a penetration enhancer and a plasticizer, respectively. Plasticizer was used to overcome film brittleness and soften the rigidity of the film structure by reducing the intermolecular forces [58]. Carbopol 940 was included as a mucoadhesive polymer. The prepared films were characterized for content uniformity, thickness, percent elongation, mucoadhesive strength and in vitro drug release. The prepared films showed a SMV content in the range of 711.81±32.82-664.29±35.60 µg and a thickness of 0.266±0.052-0.126±0.091 mm, with percentage elongation ranging from 20±2.5 to 150±10%. Mucoadhesive strength was in the range 218±17.95 to 908±69.91 N, while results of the in vitro release study illustrated a cumulative percent drug released value of 64.91±4.12 to 101.2±8.28%.

The obtained results for characterization of the prepared films indicate an adequate distribution of SMV carrier systems (inclusion complex and mixed micelles) and uniform distribution of HPMC and carbopol in the studied films as indicated from the values of film content and thickness.

Elongation percent is a character that measures the mechanical properties and the ability of the prepared films to withstand handling during manufacturing, distribution and administration. The type and percent of the film forming polymer, amount of plasticizer and drug nature have a profound effect on the elongation percent of the prepared film [29]. The ultimate film preparation should be elastic and soft enough to handle and show a satisfactory damage-resistance ability [59,60]. In this work, the prepared films showed wide variation in the elongation percent. Incorporation of carbopol during film preparation resulted in increased viscosity and formation of less elastic films. Ahmed and El-Say previously illustrated the negative effect of increasing the polymer percentage on the elongation percent of finasteride loaded transdermal films, which the authors attributed to the polymeric solution viscosity and brittleness of the prepared films, necessitating addition of more plasticizer [7].

Mucoadhesive Strength

This test was performed to measure the ability of the prepared films to interact with the buccal epithelial cells; which in turns plays an important role in the formulation absorptivity and bioavailability. Carbopol has been verified for its efficacy as a mucoadhesive polymer in pharmaceutical research. Hoffmann and Daniels evaluated the mucoadhesion of fast dissolving tablets containing carbopol and found that formulations containing carbopol showed more adhesion to mucosal surface up to three-fold compared to that without carbopol [61].

Determination of the mucoadhesion strength for the prepared nine films was achieved utilizing two methods; tensile strength and mucin particle test. Results of the tensile strength method, illustrated in table 1, were correlated to the zeta potential values obtained using the mucin particle test and used to validate this method.

In the tensile strength method, the force needed to detach the film from the biological membrane was determined. The mucoadhesion strength has been shown to be affected by hydrogen bond formation during the mucoadhesion interaction; the more hydrogen bond interaction the more elevated mucoadhesion strength produced [62]. Formulations F1, F2 and F7 showed the highest detachment force, while formulations F3, F5, and F6 exhibited the lowest force. Formulations F4, F8, and F9 demonstrated intermediate force of detachment. These observations could be directly related to the concentration of carbopol. The carboxyl groups of carbopol is expected to form hydrogen bonding with the mucin amide group of the buccal mucosa. It can be deduced that formulations containing high quantity of carbopol exhibited more adhesion due to more hydrogen bond interaction.

The mucoadhesive properties of the films was also investigated using the mucin particle test by measuring the change in zeta potential of mucin suspension after incubation with the prepared films. Data obtained was correlated to the value of the mucoadhesive strength force in order to validate the mucin particle method. Mucin is a glycoprotein complex that has a negatively charged sugars, either sialic acid or O-sulfosaccharides [63]. The carbohydrate content may account for up to 90% of the mucin weight. The polypeptide chains of mucin have domains rich in threonine and/or serine amino acids whose hydroxyl groups are in O-glycosidic linkage with oligosaccharides. The protein structure of mucin composed of two distinct regions namely; the amino- and the carboxy-ended regions that contain the amino acid cysteine which participates in the formation of disulfide linkages among and within the molecule. Previous reports indicated that pure mucin powder suspension exhibits a negative zeta potential value due to ionization of the carboxyl group [33,64]. In this work, the estimated value was found to be −9.2 mV.

Anionic polymers, such as carbopols (Polyacrylic acid derivate), are believed to form hydrogen bonds between the polymer carboxylic groups and the mucin hydroxyl groups [65]. Ion-dipole (electrostatic) interactions may also occur between carbopols and mucin [66]. Upon mixing the pure mucin powder suspension with the prepared films, the value of zeta potential has been shifted to lower values (−14.1 mV for formulations containing 5% carbopol and −19.3 mV for formulation containing 10% carbopol). The change in the zeta potential value was proportional to the concentration of carbopol in the formulation. Higher carbopol concentration demonstrated lower zeta potential value. Accordingly, the mucin particle test is in a good agreement with the tensile strength method.

In Vitro Release

Figure 8A:
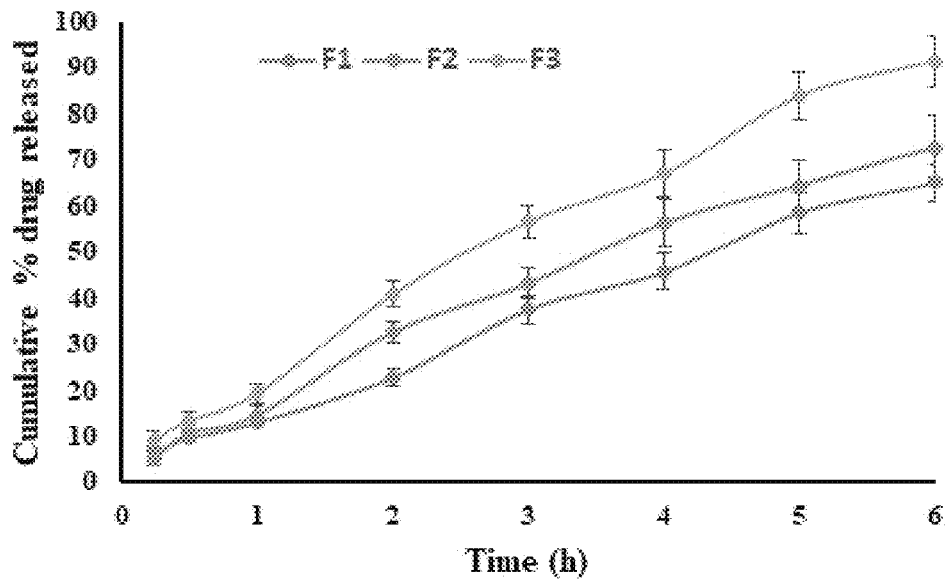
FIG. 8A-C. In vitro release of simvastatin from the prepared buccal films (A) F1-F3, (B) F4-F6, and (C) F7-F9.
Figure 8B:
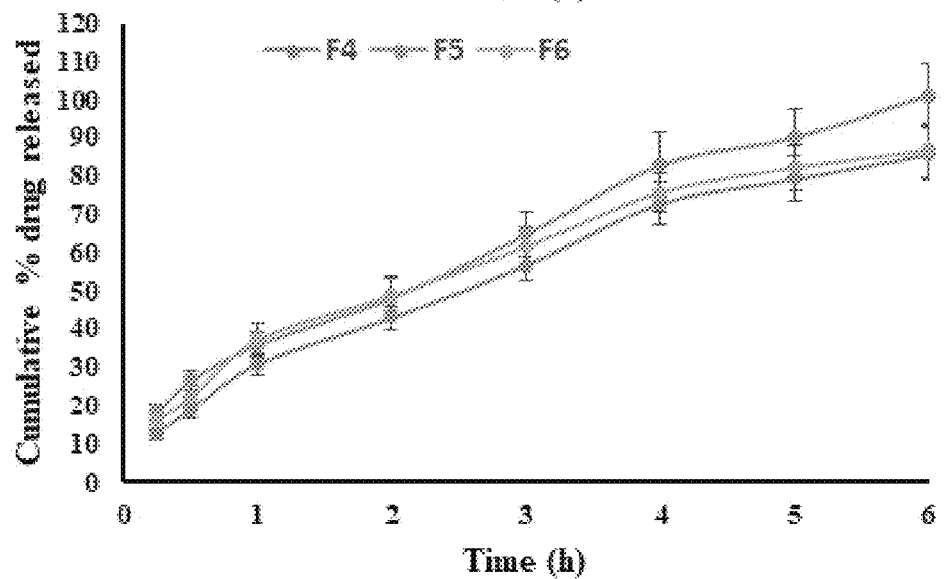
Figure 8C:
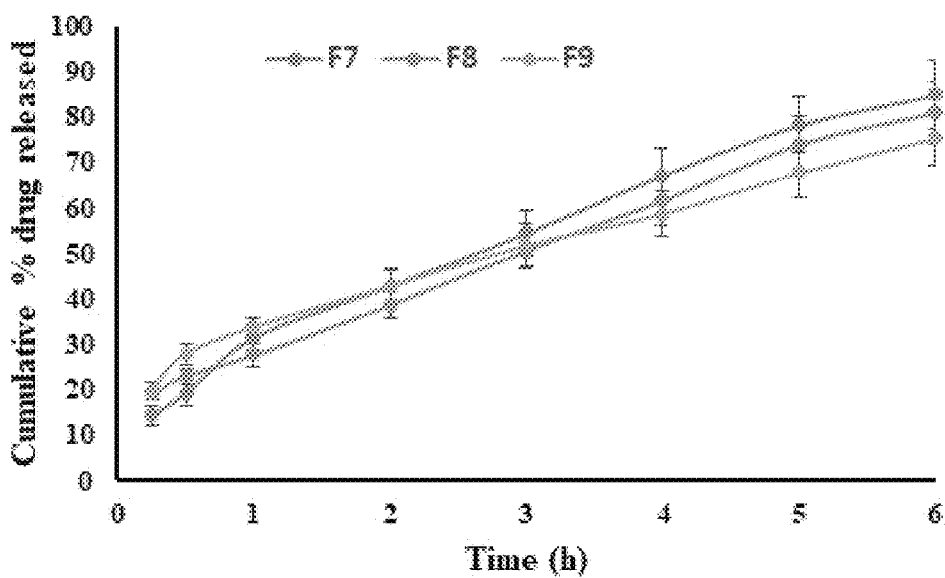

The release of SMV from the prepared buccal films is illustrated in FIG. 8A-C. SMV exhibited a constant release profile from all the studied films. The drug release was highly affected by the mixed micelles to inclusion complex ratio and to the percent of carbopol. Formulations containing high ratio of inclusion complex and high percent of carbopol showed lower drug release profile. Formulation F5, containing 2:1 ratio of mixed micelles to inclusion complex and 0% of carbopol, demonstrated a drug release of 74.65±6.12% and 101.2±8.28% after 3 and 6 h, respectively. In contrast, formulation F1, containing mixed micelles to inclusion complex ratio of 1:2 and a carbopol percent of 10%, showed a percent drug release of 37.52±3.1% and 64.91±4.12%, respectively. As previously discussed in the permeability study section, drug loaded mixed micelles carrier was superior to the inclusion complex drug carrier. Accordingly, formulation containing high ratio of the former exhibited better release profile. The effect of carbopol concentration could be related to the viscosity of the formulation. When the concentration of carbopol was increased from zero to 10%, the viscosity of the polymeric solution used to develop the buccal films was increased which leads to formation of a dense polymeric matrix film after evaporation of the solvent. This dense polymeric matrix film retards the drug release from the buccal film and so demonstrates controlled drug release profile and low cumulative percent of drug released.

Optimization of the SMV Buccal Film Formulation

A three-level experimental design was implemented to study the effect of two formulation variables affecting the cumulative percent of SMV released, the elongation percent and the mucoadhesive strength from drug loaded buccal films. Table 1 illustrates the observed and predicted values for the studied responses.

Statistical analysis for the effect of $X_1$ and $X_2$ on $Y_1$, $Y_2$ and $Y_3$ was carried out by multiple regression analysis and two-way ANOVA using the StatGraphics software. Values for the estimated effect of the studied factors, F-ratio, and the associated p-value are illustrated in Table 2. A positive estimated value indicates a synergistic effect for a variable, while a negative value is an indication of an antagonistic effect. The value of the F-ratio compares the actual and expected variations in the variable averages; an F-ratio greater than 1 is a sign of a location effect, and thus the p-value reports the significance level. A factor is considered to significantly affect the studied response if the p-value differs from 0 and is less than 0.05. The equations of the fit model were found to be:

$$Y1 = 86.7879 - 0.152569 \times X_1 - 3.87333 \times X2 + 0.00519104 \times X1^2 + 0.0164716 \times X1 \times X2 + 0.115667 \times X2^2 \quad (6)$$

$$Y2 = 26.3696 + 1.92516 \times X1 - 8.16547 \times X2 + 0.0015003 \times X1^2 - 0.120012 \times X1 \times X2 + 0.466667 \times X2^2 \quad (7)$$

$$Y3 = 796.5 - 22.2363 \times X1 + 75.5293 \times X2 + 0.202841 \times X1^2 + 0.40204 \times X1 \times X2 - 3.76667 \times X2^2 \quad (8)$$

ANOVA revealed a significant antagonistic effect of $X_1$ (mixed micelles to inclusion complex ratio, p-value=0.0054) on $Y_1$. The percent of carbopol ($X_2$) demonstrated a marked significant effect on all the studied variables. $X_2$ was antagonistically affecting $Y_1$ (p-value=0.0027) and $Y_2$ (p-value=0.0119) while it showed an agonistic effect on $Y_3$ (p-value=0.0013). The Pareto charts obtained, depicted in FIG. 9A-C, clearly confirm this finding. A vertical reference line at P-value equals 0.05 is represented. An effect that exceeds this line is an indication of a significant effect. Moreover, to study the effect of changing the levels of $X_1$ and $X_2$ on $Y_1$, $Y_2$ and $Y_3$ the estimated response surfaces were generated and are graphically represented in FIG. 9A-C. An explanation for the effect of the studied variables on each response was clarified in the above section.

TABLE 2

Estimated effects of factors, F-ratio, and associated p-value for $Y_1$-$Y_3$ of SMV-buccal films formulations.

| Factor | $Y_1$ | | | $Y_2$ | | | $Y_3$ | | |
| --- | --- | --- | --- | --- | --- | --- | --- | --- | --- |
| | Estimated effect | F-ratio | p-value | Estimated effect | F-ratio | p-value | Estimated effect | F-ratio | p-value |
| $X_1$ | 14.96 | 52.58 | 0.0054* | 49.17 | 8.09 | 0.0654 | 2.0 | 0.00 | 0.9701 |
| $X_2$ | −18.93 | 84.16 | 0.0027* | −95.0 | 30.21 | 0.0119* | 579.67 | 139.29 | 0.0013* |
| $X_1X_1$ | 2.88 | 0.65 | 0.4788 | 0.83 | 0.00 | 0.9795 | 112.67 | 1.75 | 0.2772 |
| $X_1X_2$ | 2.75 | 1.18 | 0.3569 | −20.0 | 0.89 | 0.4145 | 67.0 | 1.24 | 0.3466 |
| $X_2X_2$ | 5.78 | 2.62 | 0.2041 | 23.33 | 0.61 | 0.4926 | −188.33 | 4.90 | 0.1137 |
| $R^2$ | | 97.91% | | | 92.99% | | | 98.00% | |
| Adj-$R^2$ | | 94.45% | | | 81.30% | | | 94.67% | |
| SEE | | 2.53 | | | 21.16 | | | 60.15 | |
| MAE | | 1.29 | | | 10.49 | | | 30.48 | |

Note:

*Significant effect of factors on individual responses, p-value <0.05.

Abbreviations:

$X_1$, mixed micelle to inclusion complex ratio; $X_2$, percent of carbopol; $X_1X_1$, $X_1X_2$, and $X_2X_2$ are the interaction terms between the factors; $Y_1$, cumulative percent of drug released; $Y_2$, elongation percent; $Y_3$, mucoadhesive strength; $R^2$, R-squared; Adj-$R^2$, adjusted R-squared; SEE, standard error of estimate; MAE, mean absolute error.

Preparation and Characterization of the Optimum SMV Buccal Film Formulation

To develop an optimum SMV mucoadhesive buccal film formulation characterized by a maximum $Y_1$, $Y_2$ and $Y_3$, the optimum levels (desirability) for $X_1$ and $X_2$ were identified. Table 3 demonstrates the optimum desirability levels for the independent variables. The optimized formulation was prepared and characterized as previously described. The predicted, observed and residual values for the studied responses were depicted in Table 3.

TABLE 3

The optimum levels and desirability values of each studied factor and multiple response optimization.

| Factors | Low | High | Optimum level for each response | | | Optimum desirability level |
|---|---|---|---|---|---|---|
| | | | $Y_1$ = 99.68% | $Y_2$ = 161.38% | $Y_3$ = 826.27 N | |
| $X_1$ (Ratio) | 1:2 | 2:1 | 2:1 | 2:1 | 2:1 | 2:1 |
| $X_2$ (%) | 0 | 10 | 0 | 0 | 10 | 3.84 |

| Responses | Goal | Optimum desirability | | |
|---|---|---|---|---|
| | | Predicted values | Observed values | Residual |
| $Y_1$ (%) | Maximize | 90.73 | 92.74 | ±2.01 |
| $Y_2$ (%) | Maximize | 106.18 | 110.54 | ±4.36 |
| $Y_2$ (N) | Maximize | 553.09 | 523.41 | ±29.68 |

Abbreviations:

$X_1$, mixed micelle to inclusion complex ratio; $X_2$, percent of Carbopol; $Y_1$, cumulative percent of drug released; $Y_2$, elongation percent; $Y_3$, mucoadhesive strength.

The optimum formulation was also characterized for in vitro dissolution time and ex vivo drug release. The average dissolution time for this formulation was 8.9±2.5 minutes. Vila et al reported an in vitro dissolution time of 6.6±3.0 minutes for pure drug loaded pullan-based mucoadhesive buccal film [21]. Our result is slightly higher than reported by Vila et al due to the presence of SMV in the form of mixed micelles and inclusion complex. Results for the ex vivo permeation across the bovine buccal mucosal tissue indicated superiority of the optimized formulation loaded with mixed micelles and inclusion complex when compared to the film counterpart infused with pure drug (data not shown). The calculated results for the permeation parameters presented in table 4 also confirmed this finding. Accordingly, the optimized SMV loaded buccal film is a useful drug delivery system that exhibits dual release mechanisms from the mixed micelles and inclusion complex drug carriers. The developed films enhance SMV bioavailability due to enhanced drug aqueous solubility, improved drug permeation and avoidance of the first-pass effect from the buccal route.

TABLE 4

Permeation parameters for the release data of SMV mucoadhesive buccal films.

| Run | Jss ($\mu g/cm^2$ min) | P × $10^{-4}$ (cm/min) | D × $10^{-4}$ (cm/min) |
|---|---|---|---|
| F1 | 1.208 | 17.560 | 21.974 |
| F2 | 1.166 | 16.954 | 20.406 |
| F3 | 1.470 | 21.368 | 32.369 |
| F4 | 1.249 | 18.065 | 23.581 |
| F5 | 1.502 | 21.825 | 34.167 |
| F6 | 1.106 | 15.998 | 18.552 |
| F7 | 1.237 | 17.977 | 22.979 |
| F8 | 1.238 | 18.006 | 22.973 |
| F9 | 1.132 | 16.452 | 19.154 |
| Opt. Formulation | 1.704 | 24.159 | 42.638 |
| Pure Drug Formulation | 0.9324 | 13.552 | 12.904 |

Abbreviations:
Jss, steady state flux;
P, permeability coefficient;
D, diffusion coefficient.

As shown in Table 5, the 2:1 ratio of mixed micelles to the inclusion complex solution provided a synergistic effect. The cumulative amount of SMV permeated increased by 1.45 fold from films loaded with inclusion complex when compared to pure drug films. Moreover, films loaded with simvastatin in the form of mixed micelles demonstrated 2.1-fold increase in the drug permeation when compared to pure drug films. Interestingly, films loaded with mixed micelles and the inclusion complex at a 2:1 ratio, showed more than a 3.9-fold increase in the drug permeation.

TABLE 5

Fold increase in drug permeation from the studied films relative to pure drug film.

| | IC | MM | MM-IC (2:1) | MM-IC (1:1) | MM-IC (1:2) |
|---|---|---|---|---|---|
| fold increase | 1.45 | 2.1 | 3.9 | 3.19 | 2.44 |
| SD | 0.113 | 0.133 | 0.417 | 0.141 | 0.3889 |

Conclusions

Complexation of SMV with HP-βCD was superior to all the studied polymers and it resulted in enhancement of the drug aqueous solubility. Nano-sized SMV mixed micelles formulation was well developed and showed spherical shaped nanoparticles. Both carrier systems enhanced the drug permeation across OEC. The optimization technique was successfully implemented to develop mucoadhesive buccal films, containing different ratios of both carriers and various concentrations of carbopol, characterized by maximum percent of drug release, maximum elongation percent and higher mucoadhesive strength. A mucoadhesive buccal film loaded with SMV in the form of HP-βCD inclusion complex and mixed micelles carriers is an efficient drug delivery system with enhanced drug ex vivo permeation. The developed SMV loaded mucoadhesive buccal film enhances the drug bioavailability and is an alternative to currently available marketed SMV oral tablets.

Acknowledgment

This project was funded by the Deanship of Scientific Research (DSR) at King Abdulaziz University, Jeddah, under grant no. (RG-4-166-38). The inventors, therefore, acknowledge with thanks to DSR for technical and financial support.

REFERENCES

1. Kreatsoulas C, Anand S S. The impact of social determinants on cardiovascular disease. Can. J. Cardiol. [Internet]. Pulsus Group; 2010 [cited 2019 October 15]; 26 Suppl C:8C-13C.
2. Moghadasian M H. Clinical pharmacology of 3-hydroxy-3-methylglutaryl coenzyme a reductase inhibitors. Life Sci. [Internet]. Pergamon; 1999 [cited 2019 October 15]; 65:1329-37.
3. Parhi R, Suresh P. Formulation optimization and characterization of transdermal film of simvastatin by response surface methodology. Mater. Sci. Eng. C. Elsevier B. V.; 2016; 58:331-41.
4. Kumar S, Shen J, Burgess D J. Nano-amorphous spray dried powder to improve oral bioavailability of itraconazole. J. Control. Release. Elsevier B. V.; 2014; 192:95-102.
5. Khadka P, Ro J, Kim H, Kim I, Kim J T, Kim H, et al. Pharmaceutical particle technologies: An approach to improve drug solubility, dissolution and bioavailability. Asian J. Pharm. Sci. [Internet]. Elsevier Ltd; 2014; 9:304-16.
6. Vimalson C D, Parimalakrishnan S, Jeganathan N S, Anbazhagan S. Techniques to enhance solubility of hydrophobic drugs: An overview. Asian J. Pharm. 2016; 10:S67-75.
7. Ahmed T A, El-Say K M. Transdermal film-loaded finasteride microplates to enhance drug skin permeation: Two-step optimization study. Eur. J. Pharm. Sci. [Internet]. Elsevier B. V.; 2016; 88:246-56.
8. Ahmed T A. Preparation of finasteride capsules-loaded drug nanoparticles: formulation, optimization, in vitro, and pharmacokinetic evaluation. Int. J. Nanomedicine [Internet]. Dove Press; 2016 [cited 2016 February 13]; 11:515-27.
9. Alshahrani S M, Lu W, Park J-B, Morott J T, Alsulays B B, Majumdar S, et al. Stability-enhanced Hot-melt Extruded Amorphous Solid Dispersions via Combinations of Soluplus® and HPMCAS-HF. AAPS PharmSciTech [Internet]. Springer U S; 2015 [cited 2017 August 30]; 16:824-34.
10. Ahmed T A. Formulation and clinical investigation of optimized vinpocetine lyoplant-tabs: new strategy in development of buccal solid dosage form. Drug Des. Devel. Ther. 2019; 13:205-20.
11. Pande V V., Abhale V N. Nanocrystal technology: A particle engineering formulation strategy for the poorly water soluble drugs. Int. J. Pharm. [Internet]. Elsevier B. V.; 2013; 453:126-41.
12. Fahr A, Liu X. Drug delivery strategies for poorly water-soluble drugs. Expert Opin. Drug Deliv. [Internet]. 2007 [cited 2019 October 16]; 4:403-16.
13. Zhang D, Lee Y-C, Shabani Z, Frankenfeld Lamm C, Zhu W, Li Y, et al. Processing Impact on Performance of Solid Dispersions. Pharmaceutics [Internet]. Multidisciplinary Digital Publishing Institute (MDPI); 2018 [cited 2019 October 16]; 10.
14. Savjani K T, Gajjar A K, Savjani J K. Drug Solubility: Importance and Enhancement Techniques. ISRN Pharm. 2012; 2012:1-10.
15. Bauduin P, Renoncourt A, Kopf A, Touraud D, Kunz W. Unified Concept of Solubilization in Water by Hydrotropes and Cosolvents. Langmuir. American Chemical Society; 2005; 21:6769-75.
16. Makar R R, Latif R, Hosni E A, El Gazayerly O N. Optimization for glimepiride dissolution enhancement utilizing different carriers and techniques. J. Pharm. Investig. [Internet]. 2013; 43:115-31.
17. Badr-Eldin S M, Ahmed T A, Ismail H R. Aripiprazole-cyclodextrin binary systems for dissolution enhancement: Effect of preparation technique, cyclodextrin type and molar ratio. Iran. J. Basic Med. Sci. 2013; 16:1223-31.
18. Carrier R L, Miller L A, Ahmed I. The utility of cyclodextrins for enhancing oral bioavailability. J. Control. release. 2007; 123:78-99.
19. Rangel-Yagui C O, Pessoa A, Tavares L C. Micellar solubilization of drugs. J Pharm Pharm Sci [Internet]. 2005 [cited 2019 October 16]; 8:147-65.
20. Liu T, Wan X, Luo Z, Liu C, Quan P, Cun D, et al. A donepezil/cyclodextrin complexation orodispersible film: Effect of cyclodextrin on taste-masking based on dynamic process and in vivo drug absorption. Asian J. Pharm. Sci. [Internet]. Elsevier; 2019 [cited 2019 October 16]; 14:183-92.
21. Vila M M D C, Tardelli E R, Chaud M V., Tubino M, Balcao V M. Development of a buccal mucoadhesive film for fast dissolution: mathematical rationale, production and physicochemical characterization. Drug Deliv. [Internet]. 2014; 21:530-9.
22. Kharenko E A, Larionova N I, Demina N B. Mucoadhesive drug delivery systems (Review). Pharm. Chem. J. [Internet]. Springer U S; 2009 [cited 2019 October 16]; 43:200-8.
23. Carvalho F C, Bruschi M L, Evangelista R C, Gremião M P D. Mucoadhesive drug delivery systems. Brazilian J. Pharm. Sci. 2010; 46:1-17.
24. Seo S, Lee C-S, Jung Y-S, Na K. Thermo-sensitivity and triggered drug release of polysaccharide nanogels derived from pullulan-g-poly(l-lactide) copolymers. Carbohydr. Polym. [Internet]. Elsevier; 2012 [cited 2019 October 17]; 87:1105-11.
25. Higuchi T, Connors K. Phase Solubility Techniques. Adv. Anal. Chem. Instrum. 1965. p. 117-212.
26. Lv Q, Shen C, Li X, Shen B, Yu C, Xu P, et al. Mucoadhesive buccal films containing phospholipid-bile salts-mixed micelles as an effective carrier for Cucurbitacin B delivery. Drug Deliv. 2015; 22:351-8.
27. Ahmed T A, Badr-Eldin S M, Ahmed O A A, Aldawsari H. Intranasal optimized solid lipid nanoparticles loaded in situ gel for enhancing trans-mucosal delivery of simvastatin. J. Drug Deliv. Sci. Technol. [Internet]. Elsevier; 2018; 48:499-508.
28. El-Say K M, Ahmed T A, Badr-Eldin S M, Fahmy U, Hibah A, Ahmed O A A. Enhanced permeation parameters of optimized nanostructured simvastatin transdermal films: ex vivo and in vivo evaluation. Pharm. Dev. Technol. [Internet]. 2015; 20:919-26.
29. Dixit R P, Puthli S P. Oral strip technology: Overview and future potential. J. Control. Release [Internet]. Elsevier B. V.; 2009; 139:94-107.
30. Ahmed T A, El-Say K M. Development of alginate-reinforced chitosan nanoparticles utilizing W/O nanoemulsification/internal crosslinking technique for transdermal delivery of rabeprazole. Life Sci. [Internet]. Elsevier Inc.; 2014; 110:35-43.
31. Yu T, Andrews G, Jones D. Mucoadhesion and Characterization of Mucoadhesive Properties. Mucosal Deliv. Biopharm. Biol. Challenges Strateg. Belfast; 2014. p. 35-44.
32. Nair A B, Kumria R, Harsha S, Attimarad M, Al-Dhubiab B E, Alhaider I A. In vitro techniques to evaluate buccal films. J. Control. Release. 2013; 166:10-21.

33. Garcia M C, Aldana A A, Tártara L I, Alovero F, Strumia M C, Manzo R H, et al. Bioadhesive and biocompatible films as wound dressing materials based on a novel dendronized chitosan loaded with ciprofloxacin. Carbohydr. Polym. [Internet]. Elsevier Ltd.; 2017; 175:75-86.
34. Thongborisute J, Takeuchi H. Evaluation of mucoadhesiveness of polymers by BIACORE method and mucin-particle method. Int. J. Pharm. 2008; 354:204-9.
35. Tiwari R, Pathak K. Nanostructured lipid carrier versus solid lipid nanoparticles of simvastatin: Comparative analysis of characteristics, pharmacokinetics and tissue uptake. Int. J. Pharm. Elsevier B. V.; 2011; 415:232-43.
36. Zhang L, Liu M, Lu C, Ren D, Fan G, Liu C, et al. The hydroxypropyl-β-cyclodextrin complexation of toltrazuril for enhancing bioavailability. Drug Des. Devel. Ther. Dove Press; 2018; Volume 12:583-9.
37. Parmar K R, Patel K A, Shah S R, Sheth N R. Inclusion complexes of lamotrigine and hydroxy propyl β-cyclodextrin: Solid state characterization and dissolution studies. J. Incl. Phenom. Macrocycl. Chem. 2009; 65:263-8.
38. Mura P, Corti G, Cirri M, Maestrelli F, Mennini N, Bragagni M. Development of mucoadhesive films for buccal administration of flufenamic acid: Effect of cyclodextrin complexation. J. Pharm. Sci. [Internet]. 2010 [cited 2019 November 1]; 99:3019-29.
39. Kumria R, Harsha S, Attimarad M, Al-Dhubiab B E, Nair A B. Formulation and evaluation of nano based drug delivery system for the buccal delivery of acyclovir. Colloids Surfaces B Biointerfaces. Elsevier B. V.; 2015; 136:878-84.
40. Kumar P, Mohan C, Srinivasan M K, Shankar U, Gulati M. Physiochemical Characterization and Release Rate Studies of Solid Dispersions of Ketoconazole with Pluronic F127 and PVP K-30. Iran. J. Pharm. Res. 2011; 10:685-94.
41. Wook Jun S, Kim M-S, Kim J-S, Park H J, Lee S, Woo J-S, et al. Preparation and characterization of simvastatin/hydroxypropyl-b-cyclodextrin inclusion complex using supercritical antisolvent (SAS) process. Eur. J. Pharm. Biopharm. 2007; 66:413-21.
42. Shulman M, Cohen M, Soto-Gutierrez A, Yagi H, Wang H, Goldwasser J, et al. Enhancement of naringenin bioavailability by complexation with hydroxypropoyl-β-cyclodextrin. PLoS One. 2011; 6.
43. Doile M M, Fortunato K A, Schmücker I C, Schucko S K, Silva M A S, Rodrigues P O. Physicochemical Properties and Dissolution Studies of Dexamethasone Acetate-β-Cyclodextrin Inclusion Complexes Produced by Different Methods. AAPS PharmSciTech. 2008; 9:314-21.
44. Lodagekar A, Borkar R M, Thatikonda S, Chavan R B, Naidu V G M, Shastri N R, et al. Formulation and evaluation of cyclodextrin complexes for improved anticancer activity of repurposed drug: Niclosamide. Carbohydr. Polym. 2019; 212:252-9.
45. Furuishi T, Sekino K, Gunji M, Fukuzawa K, Nagase H, Endo T, et al. Effect of sulfobutyl ether-β-cyclodextrin and propylene glycol alginate on the solubility of clozapine. Pharm. Dev. Technol. 2019; 24:479-86.
46. Ahmed T A, Suhail M A A, Hosny K M, Abd-Allah F I. Clinical pharmacokinetic study for the effect of glimepiride matrix tablets developed by quality by design concept. Drug Dev. Ind. Pharm. [Internet]. Informa Healthcare USA, Inc; 2017; 0:1-47.
47. Ol'khovich M V., Sharapova A V., Perlovich G L, Skachilova S Y, Zheltukhin N K. Inclusion complex of antiasthmatic compound with 2-hydroxypropyl-β-cyclodextrin: Preparation and physicochemical properties. J. Mol. Liq. 2017; 237:185-92.
48. Choi S G, Lee S-E, Kang B-S, Ng C L, Davaa E, Park J-S. Thermosensitive and Mucoadhesive Sol-Gel Composites of Paclitaxel/Dimethyl-β-Cyclodextrin for Buccal Delivery. Xu B, editor. PLoS One [Internet]. Public Library of Science; 2014 [cited 2018 October 9]; 9:e109090.
49. Singh R, Bharti N, Madan J, Hiremath S N. Characterization of Cyclodextrin Inclusion Complexes—A Review. J. Pharm. Sci. Technol. 2010; 2:171-83.
50. Singh H, Philip B, Pathak K. Preparation, Characterization and Pharmacodynamic Evaluation of Fused Dispersions of Simvastatin using PEO-PPO Block Copolymer. Iran. J. Pharm. Res. 2012; 11:433-45.
51. Onyeji C O, Igbinoba S I, Oladimeji F, Soyinka J. Physicochemical characterization and dissolution properties of binary systems of pyrimethamine and 2-. African J. Biotechnol. 2009; 8:1651-9.
52. Duan Y, Wang J, Yang X, Du H, Xi Y, Zhai G. Curcumin-loaded mixed micelles: Preparation, optimization, physicochemical properties and cytotoxicity in vitro. Drug Deliv. 2015; 22:50-7.
53. Dangi J S, Vyas S P, Dixit V K. The Role of Mixed Micelles in Drug Delivery. I. Solubilization. Drug Dev. Ind. Pharm. 1998; 24:681-4.
54. Mazer N A, Benedek G B, Carey M C. Quasielastic light-scattering studies of aqueous biliary lipid systems. Mixed micelle formation in bile salt-lecithin solutions. Biochemistry [Internet]. 1980 [cited 2019 November 7]; 19:601-15.
55. Zhao L, Du J, Duan Y, Zang Y, Zhang H, Yang C, et al. Curcumin loaded mixed micelles composed of Pluronic P123 and F68: Preparation, optimization and in vitro characterization. Colloids Surfaces B Biointerfaces [Internet]. Elsevier; 2012 [cited 2019 November 7]; 97:101-8.
56. Schott H. Surfactant Systems: Their Chemistry, Pharmacy and Biology |, D. Attwood, A. T. Florence (Eds.), Chapman & Hall, London (1983), p. 794, EC4P 4EE, United Kingdom. J. Pharm. Sci. [Internet]. Elsevier; 1985 [cited 2019 November 7]; 74:1140-1.
57. Jiang T, Han N, Zhao B, Xie Y, Wang S Enhanced dissolution rate and oral bioavailability of simvastatin nanocrystal prepared by sonoprecipitation. Drug Dev. Ind. Pharm. 2012; 38:1230-9.
58. Karki S, Kim H, Na S J, Shin D, Jo K, Lee J. Thin films as an emerging platform for drug delivery. Asian J. Pharm. Sci. Elsevier B. V.; 2016; 11:559-74.
59. Perumal V A, Lutchman D, Mackraj I, Govender T. Formulation of monolayered films with drug and polymers of opposing solubilities. Int. J. Pharm. 2008; 358: 184-91.
60. Alopaeus J F, Hellfritzsch M, Gutowski T, Scherließ R, Almeida A, Sarmento B, et al. Mucoadhesive buccal films based on a graft co-polymer—A mucin-retentive hydrogel scaffold. Eur. J. Pharm. Sci. Elsevier B. V.; 2020; 142.
61. Hoffmann A, Daniels R. A novel test system for the evaluation of oral mucoadhesion of fast disintegrating tablets. Int. J. Pharm. Elsevier; 2018; 551:141-7.
62. Sudhakar Y, Kuotsu K, Bandyopadhyay A K. Buccal bioadhesive drug delivery—A promising option for orally less efficient drugs. J. Control. Release. 2006; 114:15-40.
63. Perez-vilar J, Hill R L. The Structure and Assembly of Secreted Mucins. J. Biol. Chem. 1999; 274:31751-5.
64. Onnainty R, Onida B, Páez P, Longhi M, Barresi A, Granero G. Targeted chitosan-based bionanocomposites for controlled oral mucosal delivery of chlorhexidine. Int. J. Pharm. [Internet]. 2016 [cited 2019 December 9]; 509:408-18.
65. da Silva J B, Ferreira S B de S, Reis A V, Cook M T, Bruschi M L. Assessing mucoadhesion in polymer gels: The effect of method type and instrument variables. Polymers (Basel). MDPI AG; 2018; 10.
66. Peppas N A, Huang Y. Nanoscale technology of mucoadhesive interactions. Adv. Drug Deliv. Rev. 2004. p. 1675-87.

While the invention has been described in terms of its preferred embodiments, those skilled in the art will recognize that the invention can be practiced with modification within the spirit and scope of the appended claims. Accordingly, the present invention should not be limited to the embodiments as described above, but should further include all modifications and equivalents thereof within the spirit and scope of the description provided herein.

We claim:

1. A method of improving permeation of a statin across mucosal tissue, comprising providing to a subject in need thereof a mucoadhesive buccal film comprising a crosslinked polyacrylic acid polymer, wherein the film is loaded with
   a statin-hydroxypropyl-beta-cyclodextrin inclusion complex; and
   a statin-loaded mixed micelle composition,
   wherein the ratio of the mixed micelle composition to the inclusion complex is from 2:0.5 to 2:1.5.

2. The method of claim 1, wherein the ratio of the mixed micelle composition to the inclusion complex is 2:1.

3. The method of claim 1, wherein the statin is simvastatin.

4. The method of claim 1, wherein the ratio of statin to hydroxypropyl-beta-cyclodextrin is 1:2.

5. The method of claim 1, wherein the mixed micelle composition comprises phosphatidylcholine (PC) and sodium deoxycholate (SDC).

6. The method of claim 5, wherein the ratio of PC to SDC is 1:0.8.

7. The method of claim 1, wherein the crosslinked polyacrylic acid polymer is prop-2-enoic acid.

8. The method of claim 1, wherein the crosslinked polyacrylic acid polymer is at a concentration of 3-5% w/v.

9. The method of claim 1, wherein the subject has hypercholesterolemia.

* * * * *